United States Patent
Selifonov et al.

(10) Patent No.: US 8,575,367 B2
(45) Date of Patent: Nov. 5, 2013

(54) KETAL ESTER DERIVATIVES

(75) Inventors: Sergey Selifonov, Plymouth, MN (US); Brian Daniel Mullen, Delano, MN (US); Douglas Alan Wicks, Plymouth, MN (US); Vivek Badarinarayana, St. Louis Park, MN (US)

(73) Assignee: Segetis, Inc., Golden Valley, MN (US)

( * ) Notice: Subject to any disclaimer, the term of this patent is extended or adjusted under 35 U.S.C. 154(b) by 95 days.

(21) Appl. No.: 13/120,954

(22) PCT Filed: Sep. 25, 2009

(86) PCT No.: PCT/US2009/058365
§ 371 (c)(1),
(2), (4) Date: May 23, 2011

(87) PCT Pub. No.: WO2010/036884
PCT Pub. Date: Apr. 1, 2010

(65) Prior Publication Data
US 2011/0223365 A1    Sep. 15, 2011

Related U.S. Application Data

(60) Provisional application No. 61/099,922, filed on Sep. 25, 2008, provisional application No. 61/147,278, filed on Jan. 26, 2009, provisional application No. 61/179,460, filed on May 19, 2009, provisional application No. 61/219,098, filed on Jun. 22, 2009.

(51) Int. Cl.
*C07D 319/06* (2006.01)
*C07D 407/14* (2006.01)

(52) U.S. Cl.
USPC .......................... 549/370; 549/200; 549/356

(58) Field of Classification Search
USPC ................... 549/200, 356, 369, 370
See application file for complete search history.

(56) References Cited

U.S. PATENT DOCUMENTS

| | | | |
|---|---|---|---|
| 1,934,309 A | 11/1933 | Hoover | |
| 2,004,115 A | 6/1935 | Izard et al. | |
| 2,008,720 A | 7/1935 | Lawson et al. | |
| 2,260,261 A | 10/1941 | Morey et al. | |
| 2,556,135 A * | 6/1951 | Croxall et al. | 549/372 |
| 2,654,723 A | 10/1953 | Greene | |
| 2,985,536 A | 5/1961 | Stein et al. | |
| 3,201,420 A | 8/1965 | Fuzesi et al. | |
| 3,658,789 A | 4/1972 | Fried | |
| 3,855,248 A | 12/1974 | Lannert et al. | |
| 4,105,595 A | 8/1978 | Eisenmann et al. | |
| 4,133,800 A | 1/1979 | Taubinger et al. | |
| 4,153,064 A | 5/1979 | Sawada et al. | |
| 4,205,157 A | 5/1980 | Duh | |
| 4,208,527 A | 6/1980 | Horlbeck et al. | |
| 4,460,767 A | 7/1984 | Matsumura et al. | |
| 4,737,426 A | 4/1988 | Roth | |
| 4,792,411 A | 12/1988 | Walsh | |
| 4,806,448 A | 2/1989 | Roth | |
| 4,897,497 A | 1/1990 | Fitzpatrick | |
| 5,028,667 A | 7/1991 | McLain et al. | |
| 5,095,098 A | 3/1992 | McLain et al. | |
| 5,202,413 A | 4/1993 | Spinu et al. | |
| 5,208,297 A | 5/1993 | Ford et al. | |
| 5,210,108 A | 5/1993 | Spinu et al. | |
| 5,289,384 A | 2/1994 | Akiyama | |
| 5,292,859 A | 3/1994 | Ford et al. | |
| 5,342,969 A | 8/1994 | Ford et al. | |
| 5,489,448 A | 2/1996 | Jackson et al. | |
| 5,552,513 A | 9/1996 | Bhatia | |
| 5,565,545 A | 10/1996 | Kriesche et al. | |
| 5,608,105 A | 3/1997 | Fitzpatrick | |
| 5,705,087 A * | 1/1998 | Mushrush et al. | 252/70 |
| 5,741,882 A | 4/1998 | Fujii et al. | |
| 5,859,263 A | 1/1999 | Ghorpade et al. | |
| 5,917,059 A | 6/1999 | Bruchmann et al. | |
| 5,998,092 A | 12/1999 | McCulloch et al. | |
| 6,034,118 A | 3/2000 | Bischofberger et al. | |
| 6,239,087 B1 | 5/2001 | Mao et al. | |
| 6,271,279 B1 | 8/2001 | Nodelman et al. | |
| 6,306,249 B1 | 10/2001 | Galante et al. | |
| 6,321,465 B1 | 11/2001 | Bonk et al. | |
| 6,395,810 B1 | 5/2002 | Luitjes et al. | |
| 6,528,025 B1 | 3/2003 | Boesch et al. | |
| 6,703,478 B2 | 3/2004 | Nakane et al. | |
| 6,806,392 B2 | 10/2004 | Boesch et al. | |
| 6,828,272 B2 | 12/2004 | Wiegner et al. | |
| 7,153,996 B2 | 12/2006 | Fagan et al. | |
| 7,179,775 B2 | 2/2007 | Foster | |
| 2003/0167681 A1 | 9/2003 | Delgado Puche | |

(Continued)

FOREIGN PATENT DOCUMENTS

| | | |
|---|---|---|
| CA | 1000285 | 11/1976 |
| DE | 3220035 A1 | 1/1983 |

(Continued)

OTHER PUBLICATIONS

Horsfall, et al., "Fungitoxicity of Dioxanes, Dioxolanes, and Methylenedioxybenzenes," The Connecticut Agricultrual Experiment Station New Haven, Bulletin 673: 1-44, Jun. 1965.
Patel, et al., "Ketalization of ketones with diols catalyzed by metal (IV) phosphates as solid acid catalysts," Journal of Molecular Catalysis A: Chemical 194: 267-271 (2003).
Piantadosi, et al., "The Preparation of Cyclic Glycerol Acetals by Transacetalation," Journal of the American Chemical Society 80: 6613-6617 (1958).
Preliminary Report on Patentability for International Application No. PCT/US2008/079083 dated Jan. 12, 2010.
Samacke, P., "Soy beans as polymer building blocks," (PowerPoint Presentation) (Aug. 16, 2007).
Shevchuk, et al., "Synthesis of Substituted 1,3-Dioxolanes. Part 2. Gas Chromatographic Study of the Reaction of Acetylacetone with Glycerol," Izvestiya Vysshikh Uchebnykh Zavedenii, Khimiya i Khimicheskaya Tekhnologiya 42(5) 14-15 (1999)(Russian).
Showler, et al., "Condensation Products of Glycerol with Aldehydes and Ketones. 2-Substituted m-Dioxan-5-OLS and 1,3-dioxolane-4-methanols," Chem. Rev. 67: 427-440 (1967).

(Continued)

*Primary Examiner* — Golam M M Shameem
(74) *Attorney, Agent, or Firm* — Cantor Colburn LLP

(57) ABSTRACT

The present disclosure relates to the preparation of acrylate, alkacrylate, allyl, and polycarbonate derivatives of hydroxy ketal esters, and uses thereof.

13 Claims, 12 Drawing Sheets

(56) References Cited

U.S. PATENT DOCUMENTS

| | | | |
|---|---|---|---|
| 2003/0204042 A1 | 10/2003 | Moethrath et al. |
| 2004/0010064 A1 | 1/2004 | Harashina et al. |
| 2004/0024260 A1 | 2/2004 | Winkler et al. |
| 2004/0167245 A1 | 8/2004 | Chappelow et al. |
| 2005/0101700 A1 | 5/2005 | Riebel |
| 2005/0153149 A1 | 7/2005 | Sakane et al. |
| 2006/0041156 A1 | 2/2006 | Casper et al. |
| 2006/0069230 A1 | 3/2006 | Papisov |
| 2006/0165622 A1 | 7/2006 | Hiramoto et al. |
| 2006/0207037 A1 | 9/2006 | Fadel et al. |
| 2006/0208226 A1 | 9/2006 | Maze et al. |
| 2006/0211855 A1 | 9/2006 | Doring et al. |
| 2007/0079722 A1 | 4/2007 | Parish |
| 2007/0111917 A1 | 5/2007 | Lang et al. |
| 2007/0287645 A1 | 12/2007 | Ollinger et al. |
| 2008/0124426 A1 | 5/2008 | Kobler et al. |
| 2008/0188603 A1 | 8/2008 | Porzio et al. |
| 2008/0242721 A1 | 10/2008 | Selifonov |
| 2008/0305978 A1 | 12/2008 | Wietfeldt et al. |
| 2011/0196081 A1 | 8/2011 | Kwon et al. |

FOREIGN PATENT DOCUMENTS

| | | | |
|---|---|---|---|
| DE | 10036423 A1 | 3/2001 |
| EP | 0308956 A2 | 3/1989 |
| EP | 0507190 A1 | 3/1992 |
| EP | 0913463 A1 | 5/1999 |
| FR | 1445013 | 7/1966 |
| JP | 284327 | 9/1953 |
| JP | 4217972 | 8/1992 |
| JP | 2006143702 A | 6/2006 |
| SU | 722912 | 3/1980 |
| WO | 9412489 A1 | 6/1994 |
| WO | 9640609 A1 | 12/1996 |
| WO | 03064866 A1 | 8/2003 |
| WO | 2004099173 A1 | 11/2004 |
| WO | 2005070867 A1 | 8/2005 |
| WO | 2005095378 A2 | 10/2005 |
| WO | 2005097723 A2 | 10/2005 |
| WO | 2005097724 A1 | 10/2005 |
| WO | 2006089873 A1 | 8/2006 |
| WO | 2007062118 A2 | 5/2007 |
| WO | WO2007/062118 A2 | 5/2007 |
| WO | 2007094922 A2 | 8/2007 |
| WO | 2008089463 A2 | 7/2008 |
| WO | 2008098375 A1 | 8/2008 |
| WO | 2009032905 A1 | 3/2009 |
| WO | WO2009/032905 A1 | 3/2009 |
| WO | WO2009032905 A1 | 3/2009 |
| WO | WO2009/048874 A1 | 4/2009 |
| WO | WO2010/036884 A1 | 9/2009 |
| WO | 2010151558 A1 | 12/2010 |

OTHER PUBLICATIONS

Smith, et al., "The gem-Dialkyl Effect. III. Kinetic and Equilibrium Studies of Steroid Cyclic Ketal Formation and Hydrolysis," Journal of the American Chemical Society 90(5): 1253-1257 (1968).
Sodergard, et al., "Properties of lactic acid based polymers and their correlation with composition," Prog. Polym. Sci. 27: 1123-1163 (2002).
Stern, et al., "On Hydroboration of 5-Dimethylamino-3-Methyl-1-Pentene and 5-Dimethylamino-3,3-Dimethyl-1-Pentene," Czechoslov. Chem. Commun. 39: 3538-3547 (1974).
Supplementary European Report in co-pending EP 06 83 8270 dated Nov. 12, 2009.
Takenishi, et al., The Syntheses from Levulinic Acid. A Possible Use of Some 2 Methyl-5-oxopyrrolidine-2 carboxylic Esters as Plasticizers, 27(4): 207-209 (1954).
Thompson, et al., "Characterization of Crude Glycerol from Biodiesel Production from Multiple Feedstocks," Applied Engineering in Agriculture 22(2): 261-265 (2006).
Timokhin, et al., "Levulinic acid in organic synthesis," Russian Chemical Reviews 68(1) 73-84 (1999).
Van Horn, et al., "Cross-linked and functionalized polyester materials constructed using ketoxime ether linkages," Soft Matter 3: 1032-1040 (2007).
Verlag, G., "Cargill's BiOH polyols business opens manufacturing site in Brasil," PU Magazine International Sep. 26, 2007.
Vermylen, et al., "Study of the Thermal Evolution of the Cyclic-Oligomer Formation in a Cyclic-Oligomer-Free PET," Journal of Polymer Science: Part A: Polymer Chemistry 38: 416-422 (2000).
Wang, et al., "An efficient procedure for protection of carbonyls catalyzed by sulfamic acid," Journal of Molecular Catalysis A: Chemical 233: 121-126 (2005).
Wardzinska, et al., "Influence of the Glycol Component in Dibenzoate Plasticizers on the Properties of Plasticized PVC Films," Journal of Applied Polymer Science 97: 822-824 (2005).
Wedmid, et al., "Long-Chain Stereomeric 2-Alkyl-4-methoxycarbonyl-1,3-dioxolanes in Glycerol Acetal Synthesis," J. Org. Chem. 42(22): 3624-3626 (1977).
Werpy, et al., "Top Value Added Chemicals from Biomass—vol. I—Results of Screening for Potential Candidates from Sugars and Synthesis Gas," Biomass 1-69 (2004).
Witczak, et al., "Carbohydrate Synthons in Natural Product Synthesis," ACS Symposium Series 841: 47-83 (2003).
Written Opinion for International Application No. PCT/US2008/079083 dated Jan. 22, 2009.
Wood, et al., "Cyclic polyesters: 1. Preparation by a new synthetic method, using polymer-supported reagants," Polymer 34(14): 3052-3058 (1993).
Written Opinion and Search Report from co-pending Singapore Patent Application No. 200803898-6 mailed Feb. 4, 2010.
Xu, et al., "The monoblocking of symmetrical diketones on insoluble polymer supports," Can. J. Chem. 61: 1405-1409 (1983).
Yamaguchi, Masahiko, "Synthesis of Polycyclic Aromatic Compounds via Polyketides," Yuki Gosei Kagaku Kyokaishi 45(10) 969-982 (1987) (Chinese—Translation of Abstract Only).
Yang, et al., "Investigation of homopolymerization rate of perfluoro-4,5-substituted-2-methylene-1,3-dioxolane derivatives and properties of the polymers," Journal of Flourine Science 127: 277-281 (2006).
Yang, et al., "Synthesis of acetals and ketals catalyzed by tungstosilicic acid supported on active carbon," Journal of Zhejiang University of Science 6B(5): 373-377 (2005).
Yu, et al., "Polymer blends and composites from renewable resources," Prog. Polym. Sci. 31: 576-602 (2006).
Yulan, et al., "Synthesis of Ketals of 4-Oxopentanoates," Lanzhou Daxue Xuebao, Ziran Kexueban 30(2): 66-70 (1994).
Zhang, et al., "Synthesis of Ketals of 4-Oxopentanoates," Lanzhou Daxue Xuebao, Ziran Kexueban 30(2): 66-70 (1994)(With Translation).
Zhang, et al., "Qualitative analysis of products formed during the acid catalyzed liquefaction of bagasse in ethylene glycol," Bioresource Technology 98: 1454-1459 (2007).
Fowler, et al., "The Potential Industrial Uses of Forage Grasses Including Miscanthus," BioComposites Centre, University of Wales 1-37 (2003).
Gasparrini, et al., "Synthesis of Dimethyl Acetals, Diethyl Acetals, and Cyclic Acetals Catalyzed by AminoPropylated Silica Gel Hydrochloride," Tetrahedron 40(9): 1491-1500 (1984).
Gelas, et al., "Synthese du 4-oxo et de 4-hydroxy-3,6,8-trioxabicyclo[32.1]octanes," Carbohydrate Research 30(1): 21-34 (1973) (with English abstract).
Gelas, et al., "Research in the series of the cyclic acetals XII. Synthesis of the 4-oxo and of 4-hydroxy-3,6,8-trioxasicyclo[3.2.1] Octanes," Carbohydrate Research 30(1): 21-34 (1973) (English Translation).
Gelas, et al., "Organic Chemistry. Dihydroxyl Cyclic Acetals Derived from Glycerol," C.R. Acad. Sc. Paris t. 271: Series C, 218-220 (1970) (English Translation).
Girisuta, et al., "Kinetic Study on the Acid-Catalyzed Hydrolysis of Cellulose to Levulinic Acid," Ind. Eng. Chem. Res. 46: 1696-1708 (2007).
Girisuta, et al., "Green Chemicals A Kinetic Study on the Conversion of Glucose to Levulinic Acid," Chemical Engineering Research and Design 84(A5) 339-349 (2006).

(56) References Cited

OTHER PUBLICATIONS

Gonzalez, et al., "Application of Fourier Transform Infrared Spectroscopy in the Study of Interactions Between PVC and Plasticizers: PVC/Plasticizer Compatibility versus Chemical Structure of Plasticizer," Journal of Applied Polymer Science 101: 1731-1737 (2006).
Grarbarnik, et al., "On Five- vs Six-membered Diacetal Formation from Threitol and the Intermediacy of Unusually Stable Protonated Species," J. Org. Chem. 65: 1636-1642 (2000).
Grosu, et al., "Stereochemistry and NMR Spectra of Some New Unsymmetrical Substituted 2,2-Dialkyl-1,3-Dioxanes," Revue Roumaine de Chimie 41(3-4): 259-263 (1996).
Gutsche, et al., "Reactions of Ethyl Diazoacetate with Aromatic Compounds Containing Hetero Atoms Attached to the Benzyl Carbon," J. Am. Chem. Soc. 76: 2236-2240 (1954).
Hakkarainen, Minna, "Aliphatic Polyesters: Abiotic and Biotic Degradation and Degradation Products," Advances in Polymer Science 157: 113-138 (2002).
Hall, et al., "Synthesis of a series of cyclic oligo (alkylidene isophthalate)s by cyclo-depolymerisation," Polymer 41: 1239-1249 (2000).
Haskelbhrg, L., "The preparation of glycerol esters of amino acids," Compt. rend. 190270-190272 (1930)(abstract only).
Hawker, et al., "One-Step Synthesis of Hyperbranched Dendritic Polyesters," J. Am. Chem. Soc. 113(12) 1991.
Hazimah, et al., "Recovery of Glycerol and Diglycerol from Glycerol Pitch," Journal of Oil Palm Research 15(1): 1-5 (2003).
Hegde, et al., "The Kinetics and Thermodynamics of Bicyclic Ketal Formation: An Application to the Synthesis of the Zaragozic Acids," Tetrahedron 53(32): 11179-11190 (1997).
Hense, et al., "Direct preparation of diacetals from 1,2-diketones and their use as 1,2-diol protecting groups," J. Chem. Soc. Perkin Trans. 1: 2023-2031 (1997).
Hibbert, et al., "Studies on the reactions relating to carbohydrates and polysaccharides. XVII. Structure of the isomeric methylidene glycerols," Carbohydrates and Polysaccharides 50: 3120-3127 (1928).
Hill, et al., "Studies on the reactions relating to carbohydrates and polysaccharides. XVI. Separation and identification of the isomeric ethylidene glycerols," Carbohydrates and Polysaccharides 50: 2242-2249 (1928).
Hiltunen, et al., Synthesis and Characterization of Lactic Acid Based Telechelic Prepolymers, Macromolecules 29: 8677-8682 (1996).
Hiltunen, et al., "Lactic Acid Based Poly(ester-urethanes): Use of Hydroxyl Terminated Prepolymer in Urethane Synthesis," Journal of Applied Polymer Science 8: 1091-1100 (1998).
Holland, et al., Analysis of comonomer content and cyclic oligomers of poly (ethylene terephthalate) Polymer 43: 1797-1804 (2002).
Hollingsworth, R., "Progress report for the Center of Renewable Resource Chemistries," (2007) (Powerpoint Presentation).
Hoydonckx, et al., "Esterification and transesterification of renewable chemicals," Topics in Catalysis 27(1-4): 83-96 (2004).
Imwinkelried, et al., "Diisopropyl (2S,3S)-2,3-0-Isopropylidenetartrate [1,3-Dioxolane-4,5-dicarboxylic acid, 2,2-dimethyl-, bis(1-methylethyl)ester, (4R-trans)-]," Organic Syntheses 8: 201-230 (1993).
International Search Report and Written Opinion of the International Searching Authority for International Application No. PCT/US2009/058365, International filing date: Sep. 25, 2009, date of mailing: Dec. 21, 2009, 14 pages.
International Search Report for International Application No. PCT/US20081079083 dated Jan. 22, 2009.
International Search Report for International Application No. PCT/US2008/079337 dated Apr. 21, 2009.
Kim, et al., "Preparation of High-Molecular-Weight Poly(L-lactic acid)-Based Polymers Through Direct Condensation Polymerization in Bulk State," Journal of Applied Polymer Science 100: 466-472 (2006).
Kim, et al., "Transesterification of vegetable oil to biodiesel using heterogeneous base catalyst," Catalysis Today 93-95: 315-320 (2004).

Krauskopf, Leonard G., "How About Alternatives to Phthalate Plasticizers?," Journal of Vinyl & Additive Technology 9 (4): 159-171 (2003).
Lenz, Robert W., "Structure, Properties, and Cross-linking Reactions of Poly(ester acetals)," Macromolecules 2(2): 129-136 (1969).
Li, et al., "Montmorillonite Clay Catalysis. Part 2. An Efficient and Convenient Procedure for the Preparation of Acetals Catalysed by Montmorillonite K-10," J. Chem Research (S) 26-27 (1997).
Lindblad, et al., "Polymers from Renewable Resources," Advances in Polymer Science 157: 139-161 (2002).
Lukes, Robert M., Preparation of Methyl Esters Containing the 1,3-Dioxane or 2,4,8,10-Tetroxaspiro[5.5]undecane Structure by Ketal Exchange, 26: 2515-2518 (1961).
Ma, et al., "Biodiesel production: a review," Bioresource Technology 70: 1-15 (1999).
Malmstrom, et al., "Hyberbranched Aliphatic Polyesters," Macromolecules 28: 1698-1703 (1995).
Meher, et al., "Technical aspects of biodiesel production by transesterification—a review," RSER 194: 1-21 (2004.
Meltzer, et al., "2,2-Disubstituted 1,3-Dioxolanes and 2,2-Disubstituted 1,3-Dioxanes," JOC 25: 712-715 (1960).
Meskens, Frans A.J., "Methods for the Preparation of Acetals from Alcohols or Oxiranes and Carbonyl Compounds," Synthesis 501-522 (1981).
Miller, et al., "Biorenewable Fuels and Chemicals via Reactive Distillation," Midtech Midland, May 11, 2006 ( Powerpoint Presentation).
Moeini, et al., "Preparation and Properties of Novel Green Poly(ether-ester urethane)s Insulating Coatings Based on Polyols Derived from Glycolyzed PET, Castor Oil, and Adipic Acid and Blocked Isocyanate," Journal of Applied Polymer Science 106: 1853-1859 (2007).
Moncrieff, R.W., "Ketals," The Journal of the American Oil Chemist's Society 259-261 (1947).
Nagahata, et al., "Solid-Phase Thermal Polymerization of Macrocyclic Ethylene Terephthalate Dimer Using Various Transesterification Catalysts," Journal of Polyer Science: Part A: Polymer Chemistry 38: 3360-3368 (2000).
Nagata, et al., "Synthesis and Applications of [2-Methyl-2(oxoalkyl)-1,3-dioxolan-4-yl] methyl Acrylates for Photocrosslinking Agent," Osaka Kogyo Gijutsu Shikensho Kiho 37(1): 8-16 (1986)(Translation of Abstract Only).
Nagata, et al., "Synthesis and properties of [2-methyl-2-(oxoalkyl)-1,3-dioxolan-4-yl]methyl methacrylates for photocrosslinking agent," Kobunshi Ronbunshu 42(2): 101-108 (1985)(Translation of Abstract Only).
Nakamura, et al., "Study on Ketalization Reaction of Poly (vinyl alcohol) by Ketones. IX. Kinetic Study on Acetalization and Ketalization Reaction of 1,3-Butanediol as a Model Compound for Poly (vinyl alcohol)," Polymer Science Part B: Polymer Physics 35(9): 1719-1731 (2000).
Nakamura, et al., "Study on Ketalization Reaction of Poly(vinyl alcohol) by Ketones. VIII. Kinetic Study on Acetalization and Ketalization Reactions of Poly(vinyl alcohol)," Journal of Polymer Sceince: Part A: Polymer Chemistry 34: 3319-3328 (1996).
Newman, et al., "Kinetic and Equilibrium Studies of Cyclic Ketal Formation and Hydrolysis," The Journal of the American Oil Chemist's Society 80: 6350-6355 (1958).
Olson, Edwin S., "Subtask 4.1—Conversion of Lignocellulosic Material to Chemicals and Fuels," Final Report for U.S. Dept. of Energy, National Energy Technology Laboratory, Cooperative Agreement No. DE-FC26-98FT40320 (Jun. 2001).
Ono, et al., "Biodegradation of Different Carboxylate Types of Cleavable Surfactants Bearing a 1,3,-Dioxolane Ring," JAOCS 72(7): 853-856 (1995).
Ono, et al., "Preparation, Surface-Active Properties and Acid Decomposition Profiles of a New "Soap" Bearing a 1,3-Dioxolane Ring," JAOCS 70(1): 29-36 (1993).
Ono, et al., "Synthesis and Properties of Soap Types of Double-Chain Cleavable Surfactants Derived from Pyruvate," J. Oleo Sci. 53(2): 89-95 (2004).

(56) References Cited

OTHER PUBLICATIONS

Ono, et al., "Synthesis and Properties of Soap Types of Cleavable Surfactants Bearing a 1,3-Dioxolane Ring Derived from Long-chain Epoxides and Ethyl Levulinate," J. Jpn. Oil Chem. Soc. 42(12): 965-971 (1993).
Otera, Junzo, "Esterification, Methods, Reactions, and Applications," Wiley-VCH Verlag GmbH & Co., 1-19 (2003).
Pang, et al., "Review of conventional and novel polymerization processes for polyesters," Prog. Polym. Sci. 31: 1009-1037 (2006).
Pasto, et al., "Neighboring Group Participation by Carbonyl Oxygen," Journal of the American Chemical Society 87(7): 1515-1521 (1965).
Anderson, et al., "Preparation of Carboxylic Acids from Protected Aldehydes," J. Org. Chem. 43(17): 3417-3418 (1978).
Babinsky, Ron, "PVC Additives—A Global Review," Journal of Vinyl & Additive Technology 1-4 (2007).
Bechtold, et al., "Perfectly Alternating Copolymer of Lactic Acid and Ethylene Oxide as a Plasticizing Agent for Polylactide," Macromolecules 34: 8641-8648 (2001).
Biswas, et al., "Synthesis of Diethylamine-Functionalized Soybean Oil," J. Agric. Food Chem. 53: 9485-9490 (2005).
Blee, et al., "Soybean Epoxide Hydrolase: Identification of the Catalytic Residues and Probing of the Reaction Mechanism with Secondary Kinetic Isotope Effects," The Journal of Biological Chemisty 1-33 (2004).
Boehm, R., "Knowledge on cyclic ketals. Part 11: Synthesis of some new derivatives and separation of their isomers," Pharmazie 36(5): 329-330 (1981).
Bosman, et al., "About Dendrimers: Structure, Physical Properties, and Applications," Chem. Rev. 99: 1665-1688 (1999).
Bournay, et al., "New heterogeneous process for biodiesel production: A way to improve the quality and the value of the crude glycerin produced by biodiesel plants," Catalysis Today 106: 190-192 (2005).
Bozell, et al., "Production of levulinic acid and use as a platform chemical for derived products," Resources, Conservation and Recycling 28: 227-239 (2000).
Briol, et al., "Reaction of pyroracemic acid with glycerol," Ann. 476: 215-232 (1929).
Brown, et al., "Amorphous Unsaturated Aliphatic Polyesters Derived from Dicarboxylic Monomers Synthesized by Diels-Alder Chemistry," Macromolecules 40: 4848-4853 (2007).
Brunelle, et al., "Semicrystalline Polymers via Ring-Opening Polymerization: Preparation and Polymerization of Alkylene Phthalate Cyclic Oligomers," 31: 4782-4790 (1998).
Burch, et al., "Synthesis of Cyclic Oligoesters and Their Rapid Polymerization to High Molecular Weight," Macromolecules 33: 5053-5064 (2000).
Calinaud, et al., "Cyclic acetal series. XIII. Opening of 4-oxo and 4-hydroxy-3,6,8-trioxabicyclo[3.2.1]octane and 3-pxp-2,5,7-trioxabicyclo[2.2.2]octane rings by lithium aluminum hydride and methylmagnesium iodide," Carbohydrate Research 30(1) 35-43 (1973).
Carey, et al., "Advanced Organic Chemistry, Second Edition, Part B: Reactions and Synthesis," Plenum Press 539-552 (1983).
Chang, et al., "Levulinic acid production from wheat straw," Bioresource Technology 98: 1448-1453 (2007).
Chinn, et al., "Polyether Polyols for Urethanes," SRI Consulting. Apr. 2006. Jan. 25, 2008 <http://www.sriconsulting.com/CEH/Public/Reports/688.3000/>.
Chirila, T., "Pent-and hexatomic cycloacetal esters. Synthesis and characterization of some 2-Carbalkoxymethyl-1,3-dioxolanes (dioxanes)," Revista de Chimie 28: 730-733 (1977).

Chopade, et al., "Acetalization of ethylene glycol with formaldehyde using cation-exchange resins as catalysts: batch versus reactive distillation," Reactive and Functional Polymers 34: 37-45 (1997).
Chou, et al., "A General and Improved Preparation of Monoketals of Symmetrical Diketones with Polymeric Protecting Reagant," J. Chinese Chem. Soc. 31: 87-91 (1984).
Clarkson, et al., "Continuous Reactor Technology for Ketal Formation: An Improved Synthesis of Solketal," Organic Process Research & Development 5: 630-635 (2001).
Clerici, et al., "Efficient Acetalisation of Aldehydes Catalyzed by Titanium Tetrachloride in a Basic Medium," Tetrahedron 54: 15679-15690 (1998).
Corma, et al., "Chemical Routes for the Transformation of Biomass into Chemicals," Chem. Rev. 107: 2411-2502 (2007).
Cuiling, et al., "Synthesis of Levulinic Ketals with Furfuryl Alcohol as Raw Material," Journal of Huagiao University (Nature Science) 23(3): 257-259 (2002) (English Translation).
Deslongchamps, et al., "The total synthesis of (+)-ryanodol. Part II. Model studies for rings B and C of (+)-anhydroryanodol. Preparation of a key pentacyclic intermediate," Can J. Chem. 68: 127-152 (1990).
Deutsch, et al., Investigations on heterogeneously catalysed condensations of glycerol to cyclic acetals, Journal of Catalysis 245: 428-435 (2007).
Di Serio, et al., Transesterification of Soybean Oil to Biodiesel by Using Heterogeneous Basic Catalysts, Ind. Eng. Chem. Res. 45: 3009-3014 (2006).
Gelas, et al., "Synthese du 4-oxo et de 4-hydroxy-3,6,8-trioxabicyclo[3.2.1]octanes," Carbohydrate Research 30(1): 21-34 (1973) (with English abstract).
Gelas, et al., "Research in the series of the cyclic acetals XII. Synthesis of the 4-oxo and 4-hydroxy-3,6,8-trioxasicyclo[3.2.1] Octanes," Carbohydrate Research 30(1): 21-34 (1973) (English Translation).
Garbarnik, et al., "On Five- vs Six-membered Diacetal Formation from Threitol and the Intermediacy of Unusually Stable Protonated Species," J. Org. Chem. 65: 1636-1642 (2000).
Bayer Material Science, "Plasticizers." 23 pages, Mar. 2001.
Boltorn Dendritic Polymers. Perstorp, 12 pages (2001).
Brigl, Percy, et al., "The Reaction of the Pyruvic Acid with Glycerin," Annalen der Chemie 476: p. 215-232, with English translation attached.
DuPont Tyzor Organic Titanates Technical Note—Direct Esterification, 3 pages (2001).
DuPont Tyzor Organic Titanates Technical Note—Transesterification, 3 pages (2001).
Edmunds Inc. "New twist on green: 2008 Ford Mustang seats will be soy-based foam," (2007) <http://www.edmunds.com/insideline/do/News/articleId=121682>, 3 pages.
Formvar Resin for Electron Microscopy and Other Applications; SPI Supplies; downloaded at <http://www.2spi.com> on Oct. 3, 2008, copyright 1997-2008, 4 pages.
Girisuta, Buana, "Levulinic Acid from Lignocellulosic Biomass," Rijksuniversiteit Groningen, pp. 1-148, Nov. 2007.
Holmberg, Krister, "Surfactants with controlled half-lives", Current Opinion in Colloid & Interface Science, vol. 1, Issue 5, p. 572-579, Oct. 1996.
International Preliminary Report on Patentability and Written Opinion of the International Searching Authority for PCT/US2009/058365, mailed Apr. 7, 2011, 8 pages.
Transmittal for International Preliminary Report on Patentability for International Application No. PCT/US2009/058365, mailed Apr. 7, 2011, 1 page.

\* cited by examiner

| Example No. | Compound type | Non-biomass content, g/mol | Biomass Content, g/mol | Biomass, wt% |
|---|---|---|---|---|
| 1 | Acrylate | 69 | 217 | 75.9 |
| 2 | Polyacrylate | 69 | 217 | 75.9 |
| 3 | Allyl | 101 | 217 | 68.2 |
| 4 | Epoxy | 117 | 217 | 65.0 |
| 5 | Acrylate | 201 | 128 | 38.9 |
| 6 | Allyl | 233 | 128 | 35.5 |
| 7 | Acrylate | 184 | 89 | 32.6 |
| 11 | Allyl | 131 | 301 | 69.7 |
|  |  |  |  | 86.8* |
| 13 | Allyl | 258 | 172 | 40.0 |
| 14 | Allyl | 131 | 84 | 39.1 |
|  |  |  |  | 73.5* |
| 15 | Allyl | 290 | 84 | 22.5 |
| 16 | Allyl | 158 | 89 | 36.0 |
| 17 | Glycidyl | 147 | 84 | 36.4 |
|  |  |  |  | 68.4* |
| 19 | Polycarbonate | 118 | 344 | 74.5 |
|  |  |  |  | 93.9* |
| 20 | Glycidyl | 290 | 172 | 37.2 |
| 21 | Oxiranyl polymer | 522 | 172 | 24.8 |
| 22 | Poly(carbonate urethane) | 534 | 344 | 39.2 |
|  |  |  |  | 49.4 |
| 23 | Poly(carbonate urethane) | 982 | 344 | 25.9 |
|  |  |  |  | 32.7* |

\* Reflects wt% biomass content where 1,4-butanediol and/or 1,2-propanediol are biomass based.

FIG. 11

KETAL ESTER DERIVATIVES

CROSS-REFERENCE TO RELATED APPLICATIONS

This application claims the benefit of U.S. Provisional Patent Application No. 61/099,922, entitled "Polymers from Hydroxy Ketal Carboxylates", filed on Sep. 25, 2008, which is incorporated by reference in its entirety herein; this application further claims the benefit of U.S. Provisional Patent Application No. 61/147,278, entitled "Poly(vinyl chloride) Compositions Containing Compounds Derived From Ketal Esters, and Articles Therefrom", filed on Jan. 26, 2009, which is incorporated by reference in its entirety herein; this application further claims the benefit of U.S. Provisional Patent Application No. 61/179,460, entitled "Ketal Compounds and Uses Thereof", filed on May 19, 2009, which is incorporated by reference in its entirety herein; this application further claims the benefit of U.S. Provisional Patent Application No. 61/219,098, entitled "Ketal Compounds and Uses Thereof", filed on Jun. 22, 2009, which is incorporated by reference in its entirety herein.

BACKGROUND

Many known monomers and polymers are currently synthesized from non-renewable, expensive, petroleum-derived or natural gas-derived feedstock compounds. High raw material costs and uncertainty of future supplies requires the discovery and development of useful monomers and polymers that can be made from inexpensive renewable biomass-derived feedstocks and by simple chemical methods. Using renewable resources as feedstocks for chemical processes will reduce the demand on non-renewable fossil fuels currently used in the chemical industry and reduce the overall production of carbon dioxide, the most notable greenhouse gas.

Polycarbonates, acrylate and alkacrylate monomers and polymers, allyl monomers and polymers, and oxirane (epoxy) monomers and polymers are useful materials in making many industrially important formulations and articles. It is desirable to provide acrylyl, alkacrylyl, oxiranyl, and allyl functional compounds, as well as their polymerized or grafted counterparts, based in whole or in part upon renewable biomass feedstocks. It is desirable to provide one or more linear, branched, crosslinked, or grafted materials based on renewable biomass feedstocks for use various applications in order to replace or partially replace petroleum based materials. It is desirable to provide polycarbonates based in whole or in part upon renewable biomass feedstocks, as polycarbonates are useful for many known applications. It is desirable to provide such useful materials by employing simple chemical methodology that is easily implemented using known industrial methodologies and processes.

SUMMARY

Disclosed herein are compounds including polycarbonates, allylic monomers and polymerized or grafted products thereof, oxiranyl functional monomers and polymerized or grafted products thereof, and acrylate and methacrylate monomers and polymerized or grafted products thereof, derived from renewable biomass feedstocks. The compounds are based on hydroxy ketal carboxylate Precursors, which have the structure of either Precursor P1 or Precursor P2. Precursor P1 has the structure:

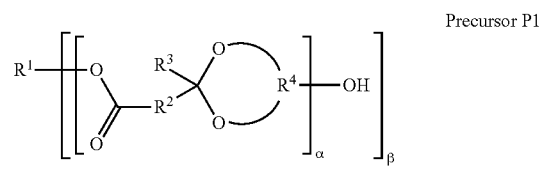

wherein $R^1$ is hydrogen or a monovalent, divalent, or multivalent linear, branched, or cyclic alkyl or alkenyl group having 1 to 36 carbon atoms, or an aryl or alkaryl group, wherein the alkyl, alkenyl, or alkaryl group includes, in some embodiments, one or more functional groups such as halogen, tertiary amine, hydroxyl, carbonate, carboxylic acid, carboxylic ester, ether, carbonyl, ketal, urethane, imide, amide, sulfone, sulfonamide, mercaptan, phosphate, phosphonooxy, silane, or silyl;

$R^2$ is a covalent bond or a linear, branched, or cyclic alkyl, alkenyl, or alkynyl group having 1 to 18 carbon atoms, or an aryl or alkaryl group, wherein the alkyl, alkenyl, aryl, or alkaryl groups include, in some embodiments, one or more additional functional groups such as halogen, tertiary amine, carbonate, ether, ester, carbonyl, urethane, imide, amide, sulfone, sulfonamide, mercapto, disulfide, phosphate, phosphonooxy, silane, or silyl;

$R^3$ is hydrogen, alkynyl, or a linear, branched, or cyclic alkyl or alkenyl group having 1 to 18 carbon atoms, or an aryl or alkaryl group, wherein the alkyl, alkenyl, aryl, or alkaryl groups include, in some embodiments, one or more additional functional groups such as halogen, tertiary amine, carbonate, ether, ester, carbonyl, urethane, imide, amide, sulfone, sulfonamide, mercapto, disulfide, phosphate, phosphonooxy, silane, or silyl;

$R^4$ is silyl, silane, or siloxane, or a hydrocarbon group having the formula

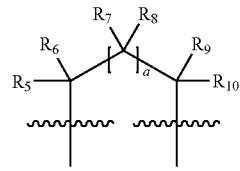

wherein a is 0 or 1 and $R^5$, $R^6$, $R^7$, $R^8$, $R^9$, and $R^{10}$ are independently hydrogen, alkynyl, or linear, branched, or cyclic alkyl or alkenyl groups having 1 to 18 carbon atoms, or an aryl or alkaryl group, wherein the alkyl, alkenyl, aryl, or alkaryl groups include, in some embodiments, one or more additional functional groups such as halogen, tertiary amine, carbonate, ether, ester, carbonyl, urethane, imide, amide, sulfone, sulfonamide, mercapto, disulfide, phosphate, phosphonooxy, silane, or silyl;

α is an integer of 1 to about 100 and, where two values of α exist on one molecule, the values of α may be the same or different; and β is an integer of about 1 to 10.

Precursor P2 has the structure:

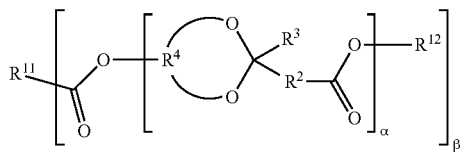
Precursor P2 wherein $R^2$, $R^3$, $R^4$, and β are as defined for Precursor P1;

$R^{11}$ is a monovalent, divalent, or multivalent linear, branched, or cyclic alkyl or alkenyl group having 1 to 36 carbon atoms, or an aryl or alkaryl group, wherein the alkyl, alkenyl, aryl, or alkaryl groups include, in some embodiments, one or more additional functional groups such as halogen, tertiary amine, carbonate, ether, carboxylic acid or ester, carbonyl, urethane, imide, amide, sulfone, sulfonamide, mercapto, disulfide, phosphate, phosphonooxy, silane, or silyl; or a ketal residue:

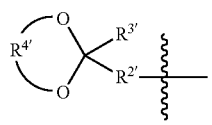

wherein $R^{2'}$, $R^{3'}$, and $R^{4'}$ are as defined for $R^2$, $R^3$, and $R^4$ respectively;

$R^{12}$ is hydrogen or a linear or branched alkyl group having between 1 and 8 carbons; and α is an integer of about 1 to 100, or where $R^{11}$ is a ketal residue α is 0 or an integer of 1 to about 100; and where there is more than one α, the values of α are the same or different.

Precursors P1 and P2 include compounds formed by the reaction of diols or triols with oxocarboxylic acids, or esters thereof, to form ketal esters and hydroxy ketal esters; in some embodiments, this is followed by self condensation to form Precursors P1 and P2 where α is 1 or more. Hydroxy ketal esters and the self-condensation products thereof are described in Selifonov, U.S. Patent Pub. No. 2008/0242721 and Wicks et al., PCT Application No. WO 2009/032905, the contents of both which are incorporated herein by reference in their entirety. Improved methods of making various ketal esters are described in Selifonov et al., PCT Application No. WO 2009/048874, the contents of which are incorporated herein by reference in its entirety. It will be understood that self-condensation of hydroxy ketal esters results in a statistical mixture of oligomeric and polymeric moieties; thus, where more than one α is present for a single Precursor P1 or P2, values of α are the same of different for each α and values of α are the same of different for each individual molecule of P1 and P2.

Precursors P1 and P2 further include products of cocondensation of hydroxy ketal esters with additional polyacids, polyols, or a combination thereof. Thus, for example, for Precursor P1 where β is 2, $R^1$ is the residue of a diol or the residue of the hydroxy-terminated condensation product of a diacid and a diol (e.g. a polyester polyol), optionally including one more hydroxy ketal esters or other difunctional monomers having both an ester or acid functionality and a hydroxyl functionality (hydroxyacids or hydroxyesters, such as lactic acid or an ester thereof) which is then further reacted with one or more hydroxy ketal esters to form the Precursor. Such cocondensation products are also described in Selifonov, U.S. Patent Pub. No. 2008/0242721 and Wicks et al., PCT Application No. WO 2009/032905. Other Precursors P1 are easily envisioned, including embodiments wherein $R^1$ is the residue of a triol and β is 3, thereby providing three hydroxyl moieties per molecule; or $R^1$ is the residue of a diol and β is 1, thereby providing two hydroxyl moieties per molecule. The Precursors P1 have in common one or more hydroxyl endgroups that are employed to make the compounds of the invention. It will be understood that each hydroxyl present on a molecule of Precursor P1 is potentially available to undergo further reaction, as described below, to form a compound of the invention. So, for example, where $R^1$ has one or more additional hydroxyl functionalities, those hydroxyls are also available, in embodiments, as precursor hydroxyls for subsequent reactions in the same manner as the hydroxy ketal hydroxyl endgroup.

Similarly, Precursor P2 includes embodiments wherein β is 2, such that $R^{11}$ is the residue of a diacid or the residue of the carboxyl-terminated condensation product of a diacid and a diol, optionally including one more hydroxy ketal esters or other difunctional monomers having both an ester or acid functionality and a hydroxyl functionality (hydroxyacids or hydroxyesters, such as lactic acid or an ester thereof) which is then further reacted with one or more hydroxy ketal esters or self condensates thereof to form the Precursor P2. Such cocondensation products are also described in Selifonov, U.S. Patent Pub. No. 2008/0242721 and Wicks et al., PCT Application No. WO 2009/032905. Other Precursors P2 are easily envisioned, including those wherein $R^{11}$ is the residue of a triacid and β is 3. The Precursors P2 have in common one or more carboxylic acid or ester endgroups that are employed to make the compounds of the invention.

Precursors P2 also include, in embodiments, the group of compounds wherein $R^{11}$ is the residue of a ketal ester. Such compounds are the condensation products of ketal esters with hydroxy ketal esters and condensates of hydroxy ketal esters. For example, where $R^{2'}$ is $-(CH_2)_2-$, $R^{3'}$ is $-CH_3$, and $R^{4'}$ is the residue of 1,2-propanediol or 1,2-ethanediol, $R^{11}$ is

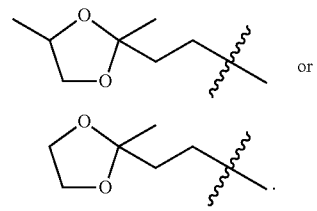

or

One example of such a condensation product is

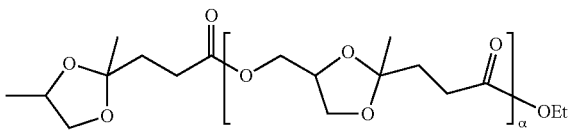

wherein α is an integer of between about 1 and 10, or in some embodiments a is between about 1 and 4. Such condensation products, and the methods to make them, are disclosed in Mullen et al., U.S. Provisional Patent Application Nos. 61/179,460 and 61/219,098. In embodiments, such Precursors P2 are plasticizers in a number of useful PVC or other polymeric compositions and, in some such embodiments, impart properties to PVC that are similar to those imparted by the commercially available plasticizer dioctyl phthalate. Other $R^{4'}$ residues suitable for the current application include any of the known 1,2- and 1,3-alkanediol compounds found in the literature. Examples of suitable 1,2- and 1,3-alkanediols include 1,2-ethanediol (ethylene glycol), 1,2-propanediol (propylene glycol), 1,3-propanediol, 2,2-dimethyl-1,3-propanediol (neopentyl glycol), 3-mercaptopropane-1,2-diol (thioglycerol), dithiothreitol, 1,2-butanediol, 1,3-butanediol, cyclohexane-1,2-diol, 1,4-dioxane-2,3-diol, 3-butene-1,2-diol, indane-1,2-diol, tartaric acid, and 2,3-dihydroxyisovaleric acid. In some embodiments, 1,2-alkanediols are synthesized by epoxidation of n-α-olefins such as 1-octene, 1-hexene, 1-decene, and the like, followed by ring opening to form the 1,2-diol. Such diols are also useful to form the alkylketal esters employed to make the compounds of the invention. Preferred diols include 1,2-propanediol and 1,2-ethanediol.

In embodiments where $R^{11}$ is a ketal residue, Precursors P2 also include the group of compounds wherein α is 0; such compounds are referred to herein as ketal esters but can also be ketal acids in embodiments where $R^{12}$ is hydrogen. The ketal esters include compounds such as

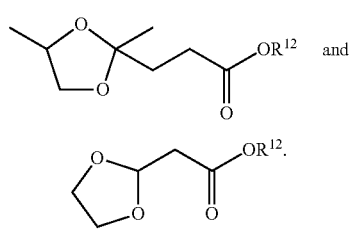

and

In some embodiments, the ketal ester embodiments of Precursor P2 are known in the literature. For example, the 1,2-propanediol ketal of ethyl levulinate is disclosed at http://www.thegoodscentscompany.com/data/rw1597311.html,

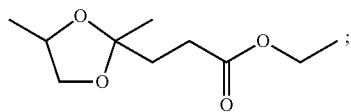

and the 1,2-propanediol ketal of ethyl acetoacetate is disclosed in Hiramoto et al., U.S. Patent Publication No. 2006/0165622,

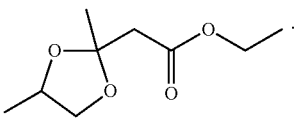

Precursors P2 also include the group of compounds wherein $R^{11}$ is the residue of a dicarboxylic acid, tricarboxylic acid, or higher polycarboxylic acid. In one such embodiment, where $R^2$ is —$(CH_2)_2$—, $R^3$ is —$CH_3$, and $R^4$ is the residue of glycerol, $R^{11}$ is the residue of adipic acid, β is 2, $R^{12}$ is —$CH_2CH_3$, α is an average of between 1 and 4, and β is 2, Precursor P2 is, in one embodiment,

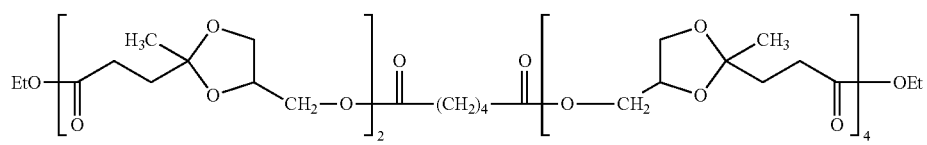

In related embodiments, α and α' are integers of between about 1 and 100, or between about 1 and 10, or between about 1 and 4. The $R^{12}$ groups have, in some embodiments, between about 1 and 8 carbons, or between about 2 and 4 carbons. The above structure is formed from the glycerol ketal of a levulinate ester, self condensed, and subsequently reacted with a diacid or an ester thereof. Such diacids include, in various embodiments, oxalic acid, malonic acid, succinic acid, adipic acid, pimellic acid, suberic acid, or sebacic acid, o, m, or p-phthalic acid, or any of the other known diacids or esters thereof. In other embodiments, triacids such as trimellitic acid and cyclohexane tricarboxylic acid are used to form a trifunctional analog of the above compounds. Higher polyacids are also employed in some embodiments of the invention, such that β, and number of carboxylic acid residues adjacent to $R^{11}$ of Precursor P2, is up to about 10. Such condensation products, and the methods to make them, are disclosed in Selifonov et al., U.S. Provisional Patent Application No. 61/147,278. In embodiments, such Precursors P2 are plasticizers in a number of useful PVC or other polymer compositions and, in some such embodiments, impart properties to PVC that are similar to those imparted by the commercially available plasticizer dioctyl phthalate.

It will be understood that each carboxylate present on a molecule of Precursor P2 is potentially available to undergo further reaction, as described below, to form a compound of the invention. So, for example, where $R^{11}$ has one or more additional carboxylic ester functionalities, those ester functionalities are also available, in embodiments, as precursor esters for subsequent reactions in the same manner as the hydroxy ketal ester endgroups of Precursor P2.

Precursors P1 and P2 are, in some embodiments, biodegradable. In various embodiments described below, the Precursors P1 and P2 enable the species of the invention to supply the desirable properties of associated with commercially useful monomers, polymers, and grafted materials and additionally supply biodegradability thereof. Additionally, Precursors P1 and P2 are capable of selective hydrolytic degradation at the ketal linkage. Ketal moieties undergo rapid and quantitative hydrolytic degradation in the presence of strong mineral acid and water using mild temperatures and pressures to produce a ketone and an alcohol. This selective degradation is accomplished, in embodiments, in the presence of other functional groups such as esters, amides, alcohols, allyl groups, acrylates, carbonates, and ethers that remain intact. The selective degradation of the ketal linkage of Precursors P1 and P2 is employed in some embodiments described below to provide additional functionality to one or more compounds of the invention, i.e. reactive ketone or hydroxyl groups for grafting reactions or compatibility and/or desired differences in hydrophilicity. Also, the chemical degradation is, in some embodiments, advantageous for lithography applications wherein a photo-acid generator (usually a strong acid) selectively cleaves the labile ketal linkage to generate hydroxyl groups or ketone groups for various applications. An additional advantage of selective degradation is that it enables, in embodiments, the breakdown of high molecular weight adducts to lower molecular weight species for ease of disposal, recyclability, and/or degradation by erosion or thermal means.

In one embodiment, the compounds of the invention are polycarbonates formed from Precursors P1 where β is 2, such that the polycarbonates have one or more repeat units of structure IA or IB:

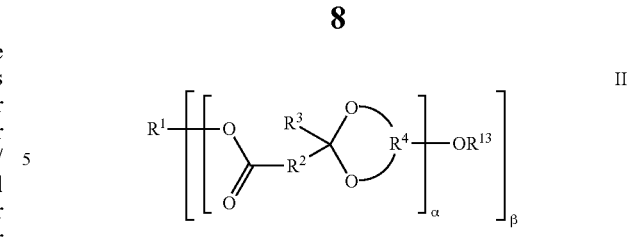

wherein
$R^1, R^2, R^3, R^4$, α, and β are as defined for Precursor P1; and
$R^{13}$ is acrylyl, alkacrylyl, glycidyl, allyl, or a linear, branched, or cyclic alkyl, aryl, or alkaryl group that includes an acrylyl, alkacrylyl, oxiranyl, or allyl moiety and can further have one or more additional functional groups that can include, for example, halogen, tertiary amine, carbonate, imide, amide, sulfone, sulfonamide, urethane, mercapto, disulfide, ether, phosphate, phosphonooxy, silane, or silyl.

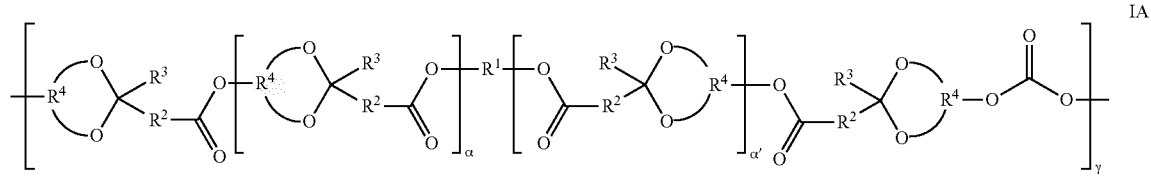

wherein
$R^1$, $R^2$, $R^3$, and $R^4$, and α are as defined for Precursor P1;
α' is 0 or an integer of about 1 to 100; and
γ is an integer of about 1 to 30.

The repeat unit corresponding to IA is formed from Precursor P1 wherein β is 2; the repeat unit corresponding to IB is formed from Precursor P1 wherein β is 1 and $R^1$ contains an hydroxyl group. The polycarbonates I have, in embodiments, endgroups that are hydroxyalkyl or alkylcarbonate. In some embodiments, the polycarbonates I having two hydroxyl endgroups and are starting materials in the synthesis of other compounds, such as poly(carbonate urethane)s. In some embodiments, Precursors P1 wherein β is more than 2 are employed to form polycarbonates I. In such embodiments, branched or crosslinked polycarbonates I are formed.

In another embodiment, the compounds of the invention are acrylyl, alkacrylyl (such as methacrylyl), oxiranyl, or allyl functional compounds having the structure II:

In yet another embodiment, the compounds of the invention are oxiranyl or allyl functional compounds having the structure III:

wherein
$R^{11}$, $R^2$, $R^3$, $R^4$, α, and β are as defined for Precursor P2; and
$R^{14}$ is glycidyl, allyl, or a linear, branched, or cyclic alkyl, aryl, or alkaryl group that includes an oxirane or allyl moiety and can further have one or more additional functional groups that can include, for example, halogen, tertiary amine, carbonate, imide, amide, sulfone, sulfonamide, urethane, mercapto, disulfide, ether, phosphate, phosphonooxy, silane, or silyl.

In yet another embodiment, the compounds of the invention are polymerized or grafted adducts formed from the compounds having the structure II. Such adducts are represented by structure IV:

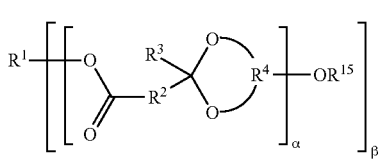

IV wherein $R^1$, $R^2$, $R^3$, $R^4$, $\alpha$, and $\beta$ are as defined for Precursor P1; and $R^{15}$ is the residue of a polymerized or grafted acrylyl, alkacrylyl, glycidyl, or allyl group, or a linear, branched, or cyclic alkyl, aryl, or alkaryl group that includes the residue of a polymerized or grafted acrylyl, alkacrylyl, oxiranyl, or allyl moiety and can further have one or more additional functional groups such as halogen, tertiary amine, carbonate, imide, amide, sulfone, sulfonamide, urethane, mercapto, disulfide, ether, phosphate, phosphonooxy, silane, or silyl.

And in yet another embodiment, the compounds of the invention are polymerized or grafted adducts formed from the compounds having the structure III. Such adducts are represented by structure V:

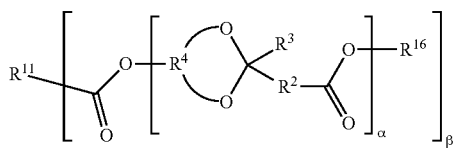

V wherein $R^{11}$, $R^2$, $R^3$, $R^4$, $\alpha$, and $\beta$ are as defined for Precursor P2; and $R^{16}$ is a repeat unit comprising the residue of a polymerized or grafted glycidyl or allyl group, or a linear, branched, or cyclic alkyl, aryl, or alkaryl group that includes the residue of a polymerized or grafted oxiranyl or allyl moiety and can further have one or more additional functional groups such as halogen, tertiary amine, carbonate, imide, amide, sulfone, sulfonamide, urethane, mercapto, disulfide, ether, phosphate, phosphonooxy, silane, or silyl.

In some embodiments, adducts IV and V are homopolymers; in other embodiments adducts IV and V are copolymers. In some embodiments adducts IV and V are incorporated into linear polymers; in other embodiments adducts IV and V are incorporated into branched polymers; in other embodiments adducts IV and V are incorporated into a crosslinked polymer network; in still other embodiments adducts IV and V are grafted to some other entity. As used herein, "entity" means either a compound or surface. Nonlimiting examples of entities include a solid macroscopic surface, such as a glass windowpane surface or a thermoplastic automobile part surface; a polymer; a coating; or a particle. In still other embodiments, adducts IV and V are both polymerized and grafted, for example where a copolymer is also grafted to a particle. Adducts IV are formed from compounds II by employing known techniques of polymerization or grafting of acrylate, alkacrylate, allyl, or oxiranyl moieties. Adducts V are formed from compounds III by employing known techniques of polymerization or grafting of allyl or oxiranyl moieties. Polymerization of compounds II and III to form adducts IV and V include, in various embodiments, one or more comonomers; thus adducts IV and V encompass copolymers thereof having incorporated therein the residues of one or more suitable comonomers.

The compounds of the invention having structures I, II, III, IV, and V are, in embodiments, made in whole or in part from materials available from renewable biomass sources. The compounds of the invention have, in embodiments, physical properties suitable for replacing petrochemical-based materials in applications wherein thermoplastics or thermosets are usefully employed. Such applications include, without limitation, coatings, films, fibers and woven or nonwoven fabrics, elastomeric members, adhesives and sealants, and monolithic articles such as lenses, food containers, furniture, and the like. Additionally, due to the biocompatibility of the major products formed on breakdown by acidic hydrolysis, these materials are useful, in some embodiments, for fabrication or coating of medical devices or as the matrix materials for controlled release of pharmaceutical or agro-chemical actives.

BRIEF DESCRIPTION OF THE DRAWINGS

FIG. 11 shows representative compounds of the invention and their biomass content.

DETAILED DESCRIPTION OF THE INVENTION

In embodiments, Precursors P1 as defined above wherein $\beta$ is 2 are useful for making one or more polycarbonates IA; in other embodiments, Precursors P1 as defined above wherein $\beta$ is 1 and $R^1$ contains at least one hydroxyl group are useful for making one or more polycarbonates IB. Collectively, polycarbonates IA and IB are referred to as "polycarbonates I." Such embodiments include polycarbonates I wherein a is 0; or wherein $\alpha$ is between about 1 and 100. Such embodiments also include polycarbonates I formed from Precursor P1 compounds wherein $\beta$ is about 3 to 10. Polycarbonates I are the reaction products of diesters of carbonic acid or phosgene ($Cl_2C\!=\!O$) with a Precursor P1 having at least two hydroxyl moieties. In some such embodiments a linear is polycarbonate formed; in other embodiments, including those wherein Precursors P1 have β of 3 or more, a branched or crosslinked structure is formed.

Figure 1:
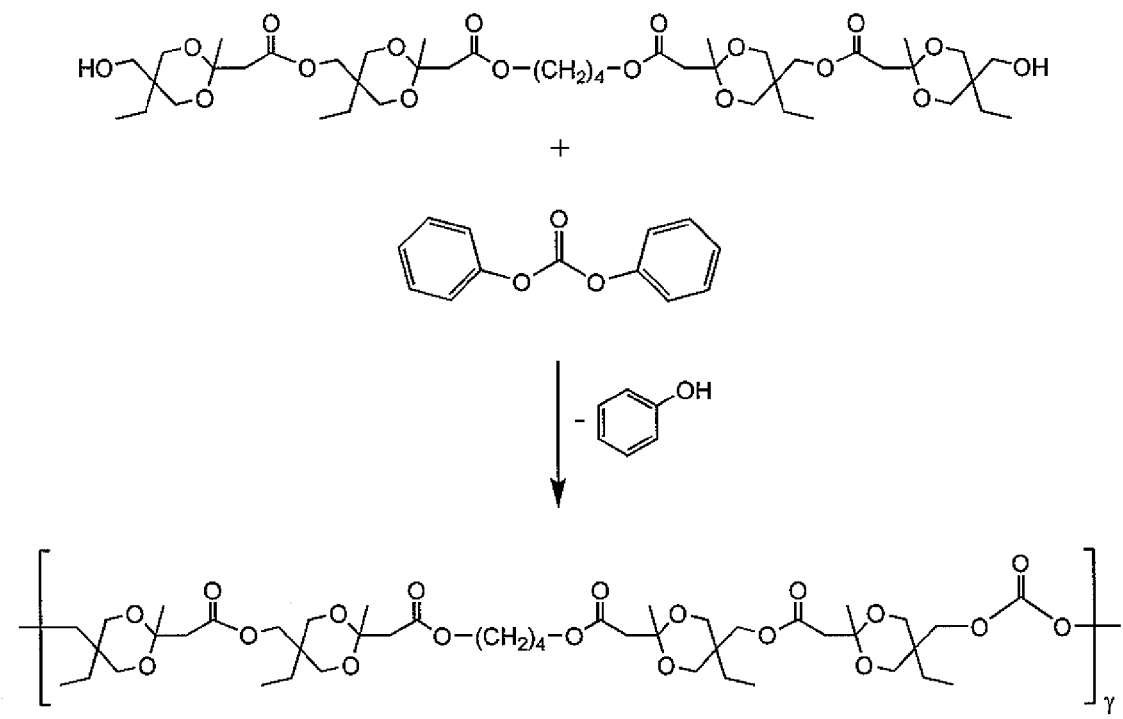
FIG. 1 shows a synthetic scheme for synthesis of a compound of the invention.

In general, any of the techniques found in the literature that are useful for making polycarbonates are also useful to make the polycarbonates of the invention. In some embodiments, a Precursor P1 compound is reacted with phosgene. In one such embodiment, the Precursor P1 is reacted with aqueous sodium hydroxide to form the corresponding sodium salt. The aqueous phase is then contacted with an immiscible organic phase containing phosgene. A linear polymer is formed, in embodiments, at the interface between the aqueous and organic phases. One example of such a reaction is represented in FIG. 1, for a Precursor P1 where a is 1, β is 2, $R^1$ is —$(CH_2)_4$—, $R^2$ is —$CH_2$—, $R^3$ is —$CH_3$, and $R^4$ is the residue of 1,1,1-trimethylolethane, or

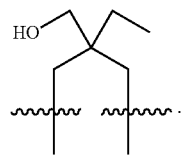 [SMILES: *CC(C*)(CC)CO]

In some such embodiments, the sodium cation is exchanged for a more organic miscible cation, such as tetrabutylammonium and the like, prior to commencing the interfacial reaction. Tetraalkylammonium cations are sometimes referred to in the literature as phase transfer catalysts, and have been observed to cause increased rates of interfacial reaction by increasing the miscibility of the salt in the organic phase. In some embodiments of the invention, employing a phase transfer catalyst with the Precursor P1 salts increases the rate of interfacial reaction to form the polycarbonates of the invention. In other embodiments, the Precursor P1 structures and their sodium salts possess sufficient organic miscibility that the use of phase transfer catalyst is not required to reach satisfactory rates of reaction.

In some embodiments, the polycarbonates of the invention are synthesized by the reaction of a Precursor P1 with a diester of carbonic acid having the general structure

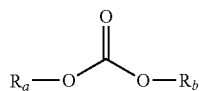

where $R_a$ and $R_b$ may be the same or different and represent optionally substituted aliphatic, ar-aliphatic or aromatic hydrocarbon radicals. The disubstituted carbonate esters can further contain heteroatoms, such as halogen, nitrogen, or oxygen. Nonlimiting examples of suitable dialkyl carbonates include dimethyl carbonate, diethyl carbonate, di-n-propyl carbonate, di-n-butyl carbonate, di-isobutyl carbonate, bis(2-bromoethyl) carbonate, bis(2,2,2-trichloroethyl)carbonate, ethyl(4-methylphenyl) carbonate, diphenyl carbonate, bis(2-methoxyphenyl)carbonate, bis(4-nitrophenyl) carbonate, dinaphthalen-1-yl carbonate, dibenzyl carbonate, and the like.

In embodiments, carbonate diesters are employed to synthesize the polycarbonates of the invention using any of the known techniques in the literature for making polycarbonates from diols or higher polyols and dialkyl carbonates or diarylcarbonates. For example, Moethrath et al., U.S. Patent Publication No. 2003/0204042 teach the synthesis of high molecular weight aliphatic polycarbonates employing a two-stage process wherein a low molecular weight aliphatic polycarbonate is formed, followed by condensation of the low molecular weight adduct with a diaryl carbonate to give a high molecular weight final product. In another example, Schnell et al., German Patent No. DE 1 031 512 disclose the synthesis of high molecular weight aliphatic polycarbonates employing diethyl carbonate and alkali catalysts in conjunction with a base-binding compound, such a phenyl chloroformate. The described methods are also useful to form the polycarbonates of the invention. One example of such a reaction is represented in FIG. 1, employing Precursor P1 where α is 1, β is 2, $R^1$ is —$(CH_2)_4$—, $R^2$ is —$CH_2$—, $R^3$ is —$CH_3$, $R^4$ is the residue of 1,1,1-trimethyloethane, and $R_a$ and $R_b$ are phenyl.

In some embodiments, the polycarbonates I of the invention have values of γ of between 1 and about 30, corresponding to molecular weights of about 500 to about 30,000 g/mol, depending on the molecular weight of Precursor P1. In various embodiments, the polycarbonates of the invention have a broad range of available properties due to the range of compounds I available, which in turn is due to the range of both structures and molecular weights of Precursor P1 compounds available. In some embodiments, the polycarbonates I possess good toughness and thermal stability. In some embodiments the polycarbonates I are transparent to visible light and possess good clarity and low color, e.g. are "water white." In some embodiments, the combination of toughness, thermal stability, and transparency make the polycarbonates I suitable for a wide range of applications.

The polycarbonates I of the invention are synthesized, in preferred embodiments, from biomass-based feedstocks. The glycerol and 1,1,1-trimethylolpropane ketals of levulinic and pyruvic acid, and esters thereof, are derivable or potentially derivable from biomass sources and do not require the use of petroleum based feedstocks. Also, carbonate precursors such as dialkylcarbonates are based in part on non-petroleum sources. In embodiments, at least 20% by weight the polycarbonates I are biomass based. In other embodiments, between about 20% and 90% by weight the polycarbonates I are biomass based. In other embodiments, between about 40% and 75% by weight the polycarbonates I are biomass based. FIG. 11 shows a list of representative compounds of the invention and their biomass content by weight.

Another advantage of the polycarbonates of the invention is that they do not require the use of Bisphenol A (4,4'-dihydroxy-2,2-diphenylpropane), the most commonly employed polycarbonate polyol. Bisphenol A has been the subject of toxicity concerns since the 1930s, particularly in food or drink contact applications (e.g., baby bottles, water/drink bottles, food containers). The polycarbonates of the invention, in one or more embodiments, are useful in applications where it is desirable to eliminate some or all of the Bisphenol A commonly employed to make polycarbonates. Additionally, the polycarbonates of the invention are, in some embodiments, biodegradable. Biodegradable polycarbonates are useful for one or more applications, for example, in food or drink contact applications, to enable disposable embodiments of various containers. Other applications where biodegradability is advantageous include disposable medical supplies such as eye shields and the like. In various embodiments, the polycarbonates of the invention advantageously supply the desirable properties of known polycarbonates and additionally supply biodegradability thereof. Additionally, the polycarbonates I of the invention are, in some embodiments, capable of selective hydrolytic degradation. In embodiments, ketal moieties undergo rapid and quantitative hydrolytic degradation in the presence of strong mineral acid and water using mild temperatures and pressures to produce a ketone moiety and an alcohol. This selective degradation may be accomplished in the presence of other functional groups such as esters, amides, alcohols, allyl groups, acrylates, carbonates, and ethers. This chemical degradation enables the break down of high molecular weight polycarbonates I to lower molecular weight species for ease of disposal, recyclability, and/or degradation by erosion or thermal means. This chemical degradation is, in embodiments, also advantageous for lithography applications of the polycarbonates I in which a photo-acid generator (usually a strong acid) selectively cleaves the labile ketal linkage to generate hydroxyl groups or ketone groups for various applications.

In some embodiments, the polycarbonates I of the invention are terminated by two hydroxyl endgroups. Such compounds I are suitable as diols for use in polyurethane synthesis. In some such embodiments, polycarbonates I having values of γ of 1 to about 30 and two hydroxyl endgroups are, in embodiments, useful as feedstocks for synthesis of polyurethanes. Such polycarbonate I diols are synthesized, in some embodiments, by controlling stoichiometry of the polycarbonate polymerization in order to provide hydroxy ketal ester functionality or hydroxyalkyl at the ends of the polycarbonate. Polycarbonates having hydroxyl endgroups are, in embodiments, reacted with one or more diisocyanates to form a polyurethane that is a poly(carbonate urethane). Poly(carbonate urethane)s of the invention are synthesized using any of the known techniques in the literature that are employed to make polyurethanes from polyols and employ known diisocyanates in the reactions. In some such embodiments, techniques used to form the poly(carbonate urethane)s of the invention are those outlined in Moore et al., *Novel Co-Polymer Polycarbonate Diols for Polyurethane Elastomer Applications*, Proceedings of the Polyurethanes Expo 2003, Oct. 1-3, 2003 (© 2003, American Chemistry Council).

Suitable diisocyanates useful in reactions with the hydroxyl groups of the polycarbonate diols of the invention include, without limitation, those represented by formula OCN—Z—NCO, in which Z represents a divalent aliphatic hydrocarbon group having 4 to 18 carbon atoms, a divalent cycloaliphatic hydrocarbon group having 5 to 15 carbon atoms, a divalent aralkyl group having 7 to 15 carbon atoms, or a divalent aromatic hydrocarbon group having 6 to 15 carbon atoms. Non-limiting examples of suitable organic diisocyanates include 1,4-tetramethylene diisocyanate, 1,6-hexamethylene diisocyanate, 2,2,4-trimethyl-1,6-hexamethylene diisocyanate, 1,12-dodecamethylene diisocyanate, cyclohexane-1,3-diisocyanate, cyclohexane-1,4-diisocyanate, 1-isocyanato-2-isocyanatomethyl cyclopentane, 1-isocyanato-3-isocyanatomethyl-3,5,5-trimethyl-cyclohexane (isophorone diisocyanate or IPDI), bis-(4-isocyanatocyclohexyl) methane, 2,4'-dicyclohexyl-methane diisocyanate, 4,4'-dicyclohexyl-methane diisocyanate, 1,3-bis-(isocyanatomethyl)-cyclohexane, 1,4-bis-(isocyanatomethyl)-cyclohexane, bis-(4-isocyanato-3-methyl-cyclohexyl)methane, α,α, α',α'-tetramethyl-1,3-xylylene diisocyanate, α,α,α',α'-tetramethyl-1,4-xylylene diisocyanate, 1-isocyanato-1-methyl-4(3)-isocyanatomethyl cyclohexane, 2,4-hexahydrotolylene diisocyanate, 2,6-hexahydrotolylene diisocyanate, 1,3-phenylene diisocyanate, 1,4-phenylene diisocyanate, 2,4-tolylene diisocyanate, 2,6-tolylene diisocyanate, 2,2'-diphenylmethane diisocyanate, 2,4'-diphenylmethane diisocyanate, 4,4'-diphenylmethane diisocyanate, 1,5-diisocyanato naphthalene; and mixtures thereof. Also suitable for reactions with polycarbonate diols are polyisocyanates containing 3 or more isocyanate groups. Nonlimiting examples of suitable polyisocyanates include 4-isocyanatomethyl-1,8-octamethylene diisocyanate, aromatic polyisocyanates such as 4,4',4''-triphenylmethane diisocyanate, and polyphenyl polymethylene polyisocyanates obtained by phosgenating aniline/formaldehyde condensates.

The Precursor P1 compounds defined above are useful, in various embodiments, for the synthesis of acrylyl or alkacrylyl compounds II. In embodiments, Precursor P1 compounds as defined above wherein β is 1 are useful for making one or more acrylyl or alkacrylyl compounds II; in other embodiments, Precursor P1 compounds as defined above wherein β is between 2 and about 10, or those wherein $R^1$ further contains one or more hydroxyl groups, are useful for making one or more acrylyl or alkacrylyl compounds II. Such embodiments include Precursor P1 compounds wherein a is 0; or wherein a is between about 2 and 100. Any of the Precursors P1 described above wherein the compound has at least one hydroxyl functionality are, in embodiments, functionalized with one or more acrylic or alkacrylic functionalities to form the acrylyl or alkacrylyl compounds of the invention. As used herein, the term "alkacryl-" means "methacryl-", "ethacryl-" or any other alkylated vinyl moiety adjacent to a carboxylate moiety, wherein the vinyl moiety is capable of subsequent addition-type initiation and propagation.

Figure 2:
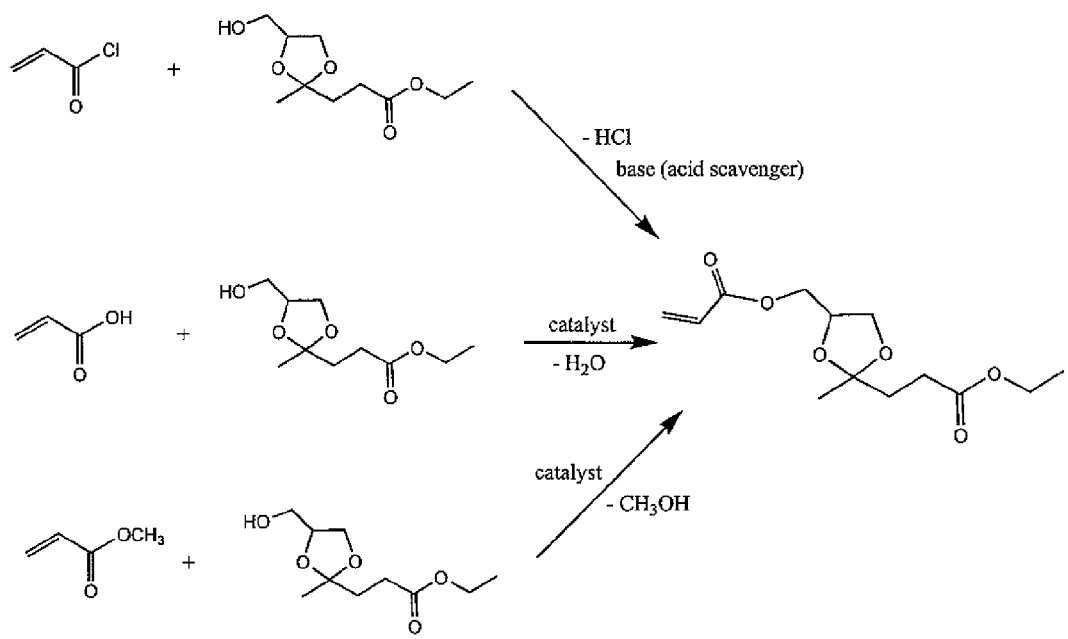
FIG. 2 shows a synthetic scheme for synthesis of a compound of the invention.

Acrylic or alkacrylic functionality is imparted, in embodiments, to the hydroxy moieties of a Precursor P1 compound by employing conventional techniques for the reaction of alkanols to form acrylates or alkacrylates. The techniques and various compounds employed in such reactions are widespread in the literature. In one embodiment, a Precursor P1 having at least one free hydroxyl group is employed in an esterification reaction with acrylic acid or alkacrylic acid to form the corresponding acrylate or alkacrylate compound II and water. In some such embodiments, a strong protic acid such as HCl, $H_2SO_4$ and the like is employed to catalyze the esterification reaction. In some such embodiments, water is removed from the reaction vessel using a known technique such as evaporation or adsorption, e.g. by molecular sieves, in order to drive the reaction to high yield. In another embodiment, acrylyl chloride or alkacrylyl chloride is reacted with a Precursor P1 having at least one free hydroxyl group to form the corresponding acrylic or alkacrylic compound II and hydrochloric acid (HCl). In some such embodiments, the HCl is scavenged by reaction with a basic compound, for example ammonia, pyridine or triethylamine, to drive the reaction toward product by removing HCl as it forms and prevent unwanted side reactions or corrosive emissions. In yet another embodiment, an ester of acrylic acid or alkacrylic acid, for example methyl acrylate or ethyl methacrylate, is transesterified with one or more hydroxyl moieties present on a Precursor P1 compound to give the acrylate or alkacrylate compound II and the corresponding alkanol. In some such embodiments, a strong protic acid (e.g. HCl, $H_2SO_4$), a Lewis acid such as a titanium (IV) alkoxide, a strong base such as a metal alkoxide (e.g. sodium methoxide) or another compound known to be a transesterification catalyst is employed to catalyze the reaction. The alkanol is, in embodiments, removed from the reaction vessel using a known technique such as evaporation or adsorption in order to drive the reaction to high yield. An example of each of these three reactions is represented in FIG. 2, for a Precursor P1 where a is 0, β is 1, $R^1$ is —$(CH_2)CH_3$, $R^2$ is —$(CH_2)_2$—, $R^3$ is —$CH_3$, and $R^4$ is the residue of glycerol.

It will easily be understood upon inspection of the Precursor P1 structure that where β is 1, a single hydroxyl moiety present on the Precursor P1 results in synthesis of a monofunctional acrylate or alkacrylate II employing one of the methodologies outlined above; and in embodiments where the Precursor P1 has β of 2 or more, and thus 2 or more hydroxyl moieties, more than one acrylic or alkacrylic functionality may be imparted to the compound II. In general, acrylates or alkacrylates II are useful for linear polymerization or copolymerization when β is 1, and are useful for branching or crosslinking reactions when β is 2 or more.

In a related reaction, Barbeau, et al., *Journal of Polymer Science Part B: Polymer Physics*, 38(21), 2750-68 (2000), disclose a reaction scheme for a compound having isocyanate endgroups that are subsequently endcapped with an acrylate group. This reaction scheme is suitably employed to form one or more compounds of the invention. Thus, in embodiments, hydroxyl moieties of a Precursor P1 may be functionalized with isocyanate groups, then further reacted with a hydroxy-functional acrylate or alkacrylate to form an acrylate or alkacrylate II. For example, in one such embodiment, a Precursor P1 having β of 1 is reacted with a diisocyanate to form a urethane moiety with a terminal isocyanate moiety; in a subsequent reaction, the terminal isocyanate is reacted with a 3-methacrylyl-2-hydroxylpropyl ester to give the corresponding acrylic prepolymer. Suitable diisocyanates useful in reactions with the hydroxyl groups of the Precursors P1 include, without limitation, those represented by formula OCN—Z—NCO and related compounds as are described above. In embodiments where the Precursor P1 has β of 2, the two hydroxyl moieties are reacted with two molar equivalents of a diisocyanate, followed by reaction with 2-hydroxypropyl acrylate to give the corresponding diacrylate. In yet another variation of this chemistry, an isocyanate endcapped material is crosslinked with a hydroxy-functional acrylate polymer, such as poly(2-hydroxypropyl acrylate) or poly(vinyl alcohol); see, for example, Decker et al., *Macromol. Mater. Eng.* 286, 5-16 (2001). Thus, in some embodiments, a Precursor P1 is isocyanate capped and then functionalized with an acrylate polymer using the method of Decker et al. or a similar method that forms one embodiment of an adduct IV of the invention.

The acrylates and alkacrylates II and adducts thereof IV of the invention are synthesized, in preferred embodiments, from biomass-based feedstocks. For example, the glycerol and 1,1,1-trimethylolpropane ketals of levulinic and pyruvic acid, and esters thereof, that form the Precursors P1 are derivable or potentially derivable from biomass sources and do not require the use of petroleum based feedstocks. Thus, the current invention enables the synthesis of a biomass based set of acrylate monomers, polymers, crosslinkers, and grafted materials; acrylate and methacrylate materials are well known to be industrially useful in a wide variety of applications. In embodiments, at least 20% by weight of the acrylates and alkacrylates II and adducts thereof IV are biomass based. In other embodiments, between about 20% and 90% by weight of the acrylates and alkacrylates II and adducts thereof IV are biomass based. In other embodiments, between about 40% and 75% by weight of the acrylates and alkacrylates II and adducts thereof IV are biomass based. FIG. 11 shows a list of representative compounds of the invention and their biomass content by weight.

The acrylates and alkacrylates II of the invention are advantageously employed in a variety of subsequent polymerization, grafting, and/or crosslinking reactions to result in a final article incorporating one or more acrylic or alkacrylic adducts IV of the invention. The polymerization, grafting, and/or crosslinking reactions are brought about by initiation and propagation of free radical, ionic, or redox reactions to result in addition products of the vinyl unsaturated moiety of the acrylyl or alkacrylyl groups, using well known and characterized reactions in the literature. Such reactions are widely used in the industry and the acrylates and alkacrylates II are, in various embodiments, reacted using any of the known techniques of polymerization or crosslinking of acrylate functionalities to form adducts IV. Numerous references are available that discuss these techniques. Radical polymerization or crosslinking reactions initiated by thermal, redox, electromagnetic radiation such as ultraviolet (UV), or electron beam (ebeam) are the most common of these known techniques. Some useful references discussing such means of polymerization of acrylate functional materials are Decker et al., *Macromol. Mater. Eng.* 286, 5-16 (2001); Burlant, W., U.S. Pat. No. 3,437,514; Endruweit, et al., *Polymer Composites* 2006, 119-128; Decker, C., *Pigment and Resin Technology* 30(5), 278-86 (2001); and Jönsson et al., *Progress in Organic Coatings* 27, 107-22 (1996). There are a number of known methods of incorporating molecules having acrylic functionality in one or more radically polymerizable formulations, e g admixing, prepolymerization to form a syrup of coatable viscosity, followed by final reaction and crosslinking, and the like. Some commonly used methods are those taught by U.S. Pat. Nos. 3,437,514; 3,528,844; 3,542,586; 3,542,587; 3,641,210; and 3,642,939. Any of the techniques employed in these references may be advantageously employed to bring about the reaction of acrylates and alkacrylates II of the invention, resulting in linear, branched, crosslinked, or grafted acrylic and alkacrylic polymers IV of the invention.

Many useful formulations employing the acrylates and alkacrylates II and adducts IV thereof are readily envisioned. For example, in one embodiment, a compound II of the invention having two or more acrylate or alkacrylate moieties is employed as a crosslinker, when blended with additional vinyl compounds, and the unsaturated sites are reacted using a known addition reaction mechanism. In other embodiments, a blend of acrylates and alkacrylates II with one or more additional vinyl compounds are provided in a formulation that is coatable, sprayable, or otherwise applied to a surface and then reacted using a known addition reaction mechanism. "Vinyl compounds" include those compounds having one or more acrylate, alkacrylate, acrylamide, or alkacrylamide residues. Non-limiting examples of additional vinyl compounds include acrylic acid, methacrylic acid, acrylamide, methacrylamide, N-hydroxymethyl acrylamide, methacryloxyethyl phosphate, acrylonitrile, methacrylonitrile, 2-acrylamido-2-methylpropanesulfonic acid and salts thereof; maleic acid, its salt, its anhydride and esters thereof; monohydric and polyhydric alcohol esters of acrylic and alkylacrylic acid such as 1,6 hexane diol diacrylate, neopentyl glycol diacrylate, 1,3 butylene dimethacrylate, ethylene glycol diacrylate, trimethylolpropane triacrylate, pentaerythritol triacrylate, pentaerythritol tetracrylate, etc.; other oxygenated derivatives of acrylic acid and alkylacrylic acids, e.g., glycidyl methacrylate, hydroxyethyl methacrylate, hydroxypropyl methacrylate, etc.; halogenated derivatives of the same, e.g., chloroacrylic acid and esters thereof; and diacrylates and dimethacrylates, e.g., ethylene glycol diacrylate. In some embodiments, the additional acrylate or alkacrylate compounds are present in blends of between about 1 and 50 mole percent with compounds II, or between about 1 and about 40 mole percent with compounds II.

"Vinyl compounds" also include non-acrylate or alkacrylate functional α,β-unsaturated compounds capable of copolymerizing with the acrylate or alkacrylate compounds II of the invention. Non-limiting examples of non-acrylate or alkacrylate functional α,β-unsaturated compounds include aromatic compounds such as styrene, methyl substituted styrenes such as α-methyl styrene, vinyl toluene, t-butyl styrene, chlorostyrene, divinyl benzene, and the like; aliphatic vinyl compounds such as ethylene, propylene, and α-olefins such as 1-octene, and the like, and allyl, bisallyl, and polyallyl compounds such as prop-2-enyl heptanoate, prop-2-enoxybenzene, prop-2-enyl acetate, allyl vinyl ether, allyl methyl ether, bisallyl ether, allyl adipate, diallyl carbonate, pentaerythritol tatraallyl ether, 1-N,4-N-bis(prop-2-enyl)benzene-1,4-dicarboxamide, and the like. Other additional vinyl compounds useful in blends with the acrylic prepolymers of the invention are divinyl and tetravinyl compounds disclosed in U.S. Pat. Nos. 3,586,526; 3,586,527; 3,586,528; 3,586,529; 3,598,530; 3,586,531; 3,591,626; and 3,595,687.

In embodiments, copolymerization of acrylates and alkacrylates II with one or more additional vinyl compounds results in acrylate and alkacrylate adducts IV that are copolymers having the residues of the one or more additional vinyl compounds incorporated therein. The properties and applications of such copolymers, as well as the biomass content thereof, are not limited in scope.

It will be easily understood that the means used to form acrylate and alkacrylate adducts IV, and blends thereof, from acrylates and alkacrylates II are not particularly limited. Thus, acrylates and alkacrylates II, or blends thereof with additional vinyl compounds, may be reacted to form linear, branched, crosslinked, or grafted acrylate and alkacrylate adducts IV using any of the known radical, redox, ionic, coordination, or group transfer polymerization techniques that are generally known in the literature. These techniques include anionic and cationic polymerization techniques; living radical polymerization techniques; coordination polymerization techniques; and group transfer polymerization techniques. Such techniques result, in embodiments, in the formation of unique and advantageous architecture, leading to desirable properties in the finished articles formed using the acrylic prepolymers of the invention. In some embodiments, the acrylates and alkacrylates II and blends containing them are processed, for example by coating, extruding, mold filling, and so forth, with or without additional solvents, prior to subsequent reaction of the acrylate or alkacrylate moieties. In some embodiments, the acrylates and alkacrylates II are blended with one or more additional acrylic compounds and/or additional vinyl compounds. After processing, the blends are reacted to form a linear, branched, crosslinked, or grafted acrylate or alkacrylate adduct IV.

In embodiments, acrylates or alkacrylates II are subjected to conditions under which they are grafted to a polymer or a surface to form grafted adducts IV. For example, Engle et al., U.S. Pat. No. 5,888,290 disclose a method of grafting acrylate polymers to silica surfaces employing chain transfer techniques in conjunction with polymerization of acrylate monomers. In another example, Bilkadi et al., U.S. Pat. No. 5,677,050 disclose a method of grafting acrylate polymers to silica surfaces employing functionalization of silica with acrylate groups in conjunction with polymerization with acrylate monomers. Such methods are useful, employing the acrylates and alkacrylates II, to provide particle grafted acrylate or alkacrylate adducts IV, but are also easily adapted to provide a grafted solid macroscopic surface, or a grafted coating surface, similarly functionalized with chain transfer agents or acrylate groups. Other techniques employed in the literature may also be used to cause acrylates or alkacrylates II to form grafted adducts IV.

The acrylate or alkacrylate adducts IV of the invention are thermosets or thermoplastics. It will be readily understood that the properties of acrylate or alkacrylate adducts IV vary greatly depending on the chemical structure of the Precursor P1 compounds used, molecular weight of the acrylate or alkacrylate adducts IV, crosslink density, and the content and structure of any additional vinyl compounds incorporated therein to form copolymers. In embodiments, formulations including acrylates or alkacrylates II include a thermal or UV reactive free radical initiator or another initiator such as an ionic or redox initiator, an additional vinyl compound, a chain transfer agent, a filler, a toughener, a solvent, a polymer, a surfactant, a UV stabilizer, a thermal stabilizer, an antioxidant, a colorant, a plasticizer, or a bleaching compound, or a combination of two or more thereof The formulations are, in embodiments, suitable for coating, spraying, thermoforming, or cutting. Formulations derived from compounds II are useful in many industrially useful applications. Such applications include formulation of sprayable, coatable, or otherwise cure-in-situ adhesives, coatings, laminates, monolithic articles such as transparent panes for window applications, films, fibers, foams, and the like. Formulations including polymerized or grafted acrylates or alkacrylate adducts IV are useful when incorporated into adhesives, coatings, laminates, monolithic articles such as transparent panes for window applications, films, fibers, foams, and the like. Such formulations are formed in either in-situ from formulation components including acrylates and alkacrylates II, or are formed by blending polymerized or grafted acrylates or alkacrylate adducts IV with one or more components such as a filler, a solvent, a polymer, a tackifier, a toughener, a surfactant, a UV stabilizer, a thermal stabilizer, an antioxidant, a colorant, a plasticizer, or a bleaching compound, or a combination of two or more thereof Blending is accomplished either before or after polymerization to form the polymerized adduct.

Additionally, the acrylates and alkacrylates II and adducts thereof IV of the invention are, in some embodiments, biodegradable. Biodegradable acrylates and alkacrylates compounds are useful for one or more applications, for example, in film applications for disposable films. Other applications where biodegradability is advantageous include disposable medical supplies such as eye shields and the like. In various embodiments, the acrylates and alkacrylates II and adducts thereof IV of the invention advantageously supply the desirable properties of known acrylate and methacrylate monomers, polymers, and grafted materials and additionally supply biodegradability thereof Additionally, the acrylates and alkacrylates II and adducts thereof IV are, in some embodiments, capable of selective hydrolytic degradation at the ketal linkage. Ketal moieties undergo rapid and quantitative hydrolytic degradation in the presence of strong mineral acid and water using mild temperatures and pressures to produce a ketone and an alcohol. This selective degradation is accomplished, in embodiments, in the presence of other functional groups such as esters, amides, alcohols, allyl groups, acrylates, carbonates, and ethers that remain intact. The selective degradation of the ketal linkage in the polymerized acrylate and alkacrylate adducts IV is employed in some embodiments to provide additional functionality to the polymer, i.e. ketone or hydroxyl groups for further grafting reactions or compatibility and/or desired differences in hydrophilicity. Also, this chemical degradation may be advantageous for lithography applications of the polymerized acrylate and alkacrylate adducts IV in which a photo-acid generator (usually a strong acid) selectively cleaves the labile ketal linkage of the acrylate and alkacrylate adducts IV to generate hydroxyl groups or ketone groups for various applications. An additional advantage of selective degradation is that it enables, in embodiments, the breakdown of high molecular weight adducts to lower molecular weight species for ease of disposal, recyclability, and/or degradation by erosion or thermal means.

The Precursors P1 are useful, in various embodiments, in the synthesis of allyl compounds II. As used herein, the term "allyl" or "allyl functionality" means a —$CH_2$—CH=$CH_2$ moiety that is capable of subsequent polymerization or crosslinking reactions utilizing a free radical mechanism. Such embodiments include those employing Precursor P1 compounds wherein a is 0 or wherein a is between about 1 and 100. Such embodiments also include Precursor P1 compounds wherein β is 1; or wherein β is about 2 to 10.

In some embodiments, the one or more hydroxyl moieties of Precursor P1 are functionalized with isocyanate groups, then further reacted with allyl alcohol to form an allyl terminated compound II. For example, in one such embodiment, a Precursor P1 having β of 2 is reacted with two equivalents of a diisocyanate to form two urethane linkages having two terminal isocyanate moieties; in a subsequent reaction, the terminal isocyanates are reacted with allyl alcohol to give the corresponding oxiranyl compound II. Suitable diisocyanates useful in reactions with the hydroxyl groups of the Precursors P1 include, without limitation, those represented by formula OCN—Z—NCO and related compounds as are described above. In another embodiment, the one or more hydroxyl moieties of Precursor P1 are reacted with allyl chloroformate to give the allylcarbonate adduct of P1. In embodiments, such reactions are carried out without an external catalyst; however, it is advantageous in such embodiments to employ a trialkylamine or pyridinium compound, such as triethylamine or pyridine, to scavenge the HCl that is a product of the addition reaction.

Precursor P2 compounds are also useful, in various embodiments, in the synthesis of allyl compounds III. Such embodiments include Precursor P2 compounds wherein α is 0 or wherein α is between about 1 and 100. Such embodiments also include Precursor P2 compounds wherein β is 1; or wherein β is about 2 to 10. Allyl alcohol is employed, in embodiments, to synthesize allyl esters III from one or more Precursors P2 by esterification or transesterification reaction using any of the known techniques commonly employed to esterify or transesterify a carboxylic acid or ester thereof with an alcohol. For example, allyl alcohol is employed in a esterification reaction of Precursor P2 wherein $R^{12}$ is hydrogen, and/or wherein $R^{11}$ further comprises a carboxylic acid moiety, by employing the methods of Kropa, U.S. Pat. No. 2,249, 768. In other embodiments, allyl alcohol is employed in the transesterification of a Precursor P2 wherein $R^{12}$ is a linear or branched alkyl group having between 1 and 8 carbons and/or wherein $R^{11}$ further comprises a carboxylic ester moiety. Suitable methods of transesterification to form allyl esters III from Precursors P2 are disclosed in Remme et al., *Synlett* 2007, 3, 491-3 and Ruszkay et al., U.S. Pat. No. 5,710,316; other suitable methods are disclosed in Singh et al., *J. Org. Chem.* 2004, 69, 209-12 and Chavan et al., *Synthesis* 2003, 17, 2695-8. Allyl monohalides are also suitably employed, in some embodiments, to synthesize compounds III from Precursors P2 by employing a palladium halide or platinum halide catalyst, as disclosed by Brady, U.S. Pat. No. 3,699, 155.

The allyl compounds II and III are, in embodiments, polymerized, copolymerized, or grafted to form adducts IV and V, respectively, using any of the techniques known in the literature to polymerize or graft allyl functional monomers. In embodiments, formulations comprising allyl compounds II and III include a free radical initiator, an additional vinyl compound as defined above, a chain transfer agent, a filler, a solvent, a polymer, a surfactant, a UV stabilizer, a thermal stabilizer, an antioxidant, a colorant, a plasticizer, or a bleaching compound, or a combination of two or more thereof. The formulations thereby formed are, in embodiments, suitable for coating, spraying, thermoforming, or cutting. Formulations derived from allyl compounds II and III are useful in many applications. Such applications include formulation of sprayable, coatable, or otherwise cure-in-situ adhesives, coatings, laminates, monolithic articles such as transparent panes for window applications, films, fibers, foams, and the like. In some embodiments, heating an allyl compound II and optionally one or more additional vinyl monomers in the presence of a thermal free-radical initiator results in an allyl adduct IV; similarly, heating an allyl compound III and optionally one or more additional vinyl monomers in the presence of a thermal free-radical initiator results in an allyl adduct V. Typically, allyl polymers are made by charging one or more allyl monomers and a free-radical initiator to a reactor, and heating the mixture at a temperature effective to polymerize the monomer. This approach is disclosed, for example, in "Kirk-Othmer Encyclopedia of Chemical Technology," $4^{th}$ ed., Volume 2, pp. 161-179. Improved methods of polymerizing allyl compounds are also usefully employed with the allyl compounds II and III of the invention. For example, U.S. Pat. No. 5,420,216 discloses that gradual addition of initiator is key to high conversion in allyl polymerization. Any such techniques may be employed to form linear, branched, crosslinked, or grafted allyl adducts IV or V from allyl compounds II and III, respectively. Grafting of allyl compounds II and III to give grafted allyl adducts IV and V are accomplished, in some embodiments, employing the techniques similar to those employed to graft acrylate compounds to particles and surfaces as disclosed in Engle et al., U.S. Pat. No. 5,888,290 and Bilkadi et al., U.S. Pat. No. 5,677,050, or other techniques employed in the literature.

In some embodiments of the invention, allyl compounds II or III have β=1, such that there is one allyl moiety per molecule; in other embodiments of the invention allyl compounds II or III have β=1 and $R^{11}$ includes an allyl ester, such that there are two allyl moieties per molecule. In some such embodiments the compounds II and III have sufficient reactivity to provide high conversion or high molecular weight in the resulting allyl polymeric or grafted adduct IV or V. In other embodiments, allyl compounds II or III have β=2 or more, such that there are at least two allyl moieties per molecule. In some embodiments the allyl compounds II or III yield a solid, high molecular weight allyl adduct IV or V by initiation with a suitable free-radical initiator. Such embodiments are useful to provide, for example, heat-resistant cast sheets and thermoset moldings. In some such embodiments, the reactivity of compounds having more than one allyl group per molecule of allyl compound II or III facilitates formation of allyl adducts IV or V in two stages: a solid allyl compound II or III is molded by heating; then completion of the heat cycle gives an allyl adduct IV or V of superior heat resistance. In embodiments, the relatively slow rate of reaction encountered with allyl groups compared to e.g. the polymerization of vinyl or acrylate groups allows for greater control of the reaction, to result in soluble "prepolymers", e.g. partially reacted hybrid molecules having chemical moieties attributable to both compounds II and IV, or III and V; that is, the hybrid molecules are partially polymerized and contain some reactive double bonds and some polymerized adducts. Allyl adducts IV and V of the invention are thermoset or thermoplastic, depending on the degree of crosslinking. It is readily understood that the properties of allyl adducts IV and V vary greatly depending on both the chemical structure of the Precursor P1 or P2 compounds used, molecular weight of the allyl adducts IV and V, crosslink or grafting density, and structure and content of any additional vinyl compound residues incorporated into allyl copolymer adducts IV and V.

One useful embodiment of the allyl compounds II and III of the invention employs minor proportions of polyfunctional allyl compounds II and III, wherein β is 2 or more, for cross-linking or curing preformed vinyl-type polymers via grafting mechanism. Among the preformed polymers cured by minor additions of polyfunctional allyl compounds and catalyst, followed by heat or irradiation, are polyethylene, PVC, and acrylonitrile-butadiene-styrene (ABS) copolymers. In other embodiments, small proportions of mono- or polyfunctional allyl compounds II or III are added as regulators or modifiers of vinyl polymerization for controlling molecular weight and polymer properties. In yet other embodiments, allyl compounds II and III having β is 2 or more are stabilizers against oxidative degradation and heat discoloration of polymers into which they are incorporated. A useful embodiment of thermoset allyl adducts IV and V of the invention is in moldings and coatings for electronic devices requiring high reliability under long-term adverse environmental conditions. These devices include electrical connectors and insulators in communication, computer, and aerospace systems. Other embodiments are readily envisioned. Formulations for applications such as those above, for example, typically include additional one or more materials such as a filler, a solvent, a polymer, a surfactant, the residue of a crosslinker, a UV stabilizer, a thermal stabilizer, an antioxidant, a toughener, a colorant, a plasticizer, or a bleaching compound, or a combination thereof.

The allyl compounds II and III and allyl adducts IV and V of the invention are synthesized, in preferred embodiments, from biomass-based feedstocks. For example, the glycerol and 1,1,1-trimethylolpropane ketals of levulinic and pyruvic acid, and esters thereof, that form the Precursors P1 and P2 are derivable or potentially derivable from biomass sources and do not require the use of petroleum based feedstocks. Thus, the current invention enables the synthesis of a biomass based set of allyl compounds II and III and polymers, crosslinkers, and grafted materials made from them; allyl materials are well known to be industrially useful in a wide variety of applications. In embodiments, at least 20% by weight of allyl compounds II and III and allyl adducts IV and V are biomass based. In other embodiments, between about 20% and 90% by weight of the allyl compounds II and III and allyl adducts IV and V are biomass based. In other embodiments, between about 40% and 75% by weight of the allyl compounds II and III and allyl adducts IV and V are biomass based. FIG. 11 shows a list of representative compounds of the invention and their biomass content by weight. Additionally, the allyl compounds II and III and adducts thereof IV and V of the invention are, in some embodiments, biodegradable. Biodegradable allylic compounds are useful for one or more applications, for example, in biodegradable cladding of cables and other items. In various embodiments, the allyl compounds II and III and adducts thereof IV and V of the invention advantageously supply the desirable properties of known allylic monomers, polymers, and grafted materials and additionally supply biodegradability thereof. Additionally, the allyl compounds II and III and adducts thereof IV and V are, in some embodiments, capable of selective hydrolytic degradation at the ketal linkage. Ketal moieties undergo rapid and quantitative hydrolytic degradation in the presence of strong mineral acid and water using mild temperatures and pressures to produce a ketone and an alcohol. This selective degradation is accomplished, in embodiments, in the presence of other functional groups such as esters, amides, alcohols, allyl groups, acrylates, carbonates, and ethers that remain intact. The selective degradation of the ketal linkage in the allyl adducts IV and V is employed in some embodiments to provide additional functionality to the polymer, i.e. ketone or hydroxyl groups for further grafting reactions or compatibility and/or desired differences in hydrophilicity. Also, this chemical degradation may be advantageous for lithography applications of the allyl adducts IV and V in which a photo-acid generator (usually a strong acid) selectively cleaves the labile ketal linkage of the allyl adducts IV and V to generate hydroxyl groups or ketone groups for various applications. An additional advantage of selective degradation is that it enables, in embodiments, the breakdown of high molecular weight adducts to lower molecular weight species for ease of disposal, recyclability, and/or degradation by erosion or thermal means.

The Precursors P1 defined above are useful, in embodiments, for the synthesis of glycidyl compounds II. Such embodiments include Precursor P1 compounds wherein a is 0 or wherein a is between about 1 and 100. Such embodiments also include Precursor P1 compounds wherein β is 1; or wherein β is about 2 to 10. In embodiments, an epihalohydrin, such as epichlorohydrin, is used to functionalize a Precursor P1 compound by reacting with one or more hydroxyl moieties to form a glycidyl ether. The reaction between an alcohol and epihalohydrin to form a glycidyl ether, for example the reaction of the alcohol Bisphenol A with epichlorohydrin, is known in the literature. Any of the known literature methods of forming glycidyl ethers from epihalohydrins and alcohols are advantageously employed in one or more embodiments of the invention to form one or more glycidyl compounds II. Andrews et al., U.S. Pat. No. 5,420,312 disclose another technique usefully adapted to form glycidyl compounds II.

Precursor P2 compounds are useful, in embodiments, for the synthesis of glycidyl compounds III. Such embodiments include Precursor P2 compounds wherein a is 0 or wherein a is between about 1 and 100. Such embodiments also include Precursor P2 compounds wherein β is 1, or wherein β is about 2 to 10. In some embodiments of Precursor P2 wherein $R^{12}$ is hydrogen and/or one or more carboxylic acid groups are present on $R^{11}$, glycidyl alcohol is used to synthesize glycidyl compounds III by esterification. In embodiments of Precursor P2 wherein $R^{12}$ is an alkyl group and/or one or more carboxylic ester groups are present on $R^{11}$, glycidyl alcohol is used to synthesize glycidyl compounds III by transesterification. Esterification and transesterification are accomplished using any of the known techniques commonly employed in the literature. For example, Chanda, M. and Roy, S., eds., *Plastics Technology Handbook*, $4^{th}$ ed., © 2007 Taylor & Francis Group, LLC, pp. 4-114 to 4-116; and U.S. Pat. No. 5,536,855 describe some of the methods that are useful, in embodiments, to react one or more Precursors P2 with glycidyl alcohol.

In some embodiments where $R^{12}$ of Precursor P2 is hydrogen and/or one or more carboxylic acid groups are present on $R^{11}$, epichlorohydrin is reacted directly with the carboxylic acid functionality to form the corresponding glycidyl compound III; the reaction involves ring opening of the glycidyl moiety, followed by dehydrochlorination to re-form the oxirane ring similarly to the reaction of epichlorohydrin with an alcohol. Such a reaction is carried out, in one or more embodiments, by employing the techniques of Bukowska, et al., *J. Chem. Tech. and Biotech.*, 74: 1145-1148 (1999); Otera et al., Synthesis (12), 1019-1020 (1986); Dukes et al., U.S. Pat. No. 3,576,827; Henkel & Cie G.m.b.H., British Patent No. GB 884,033; and Heer et al., German Patent Appl. No. DE 15945/70; or by other techniques found in the literature.

Figure 3A:
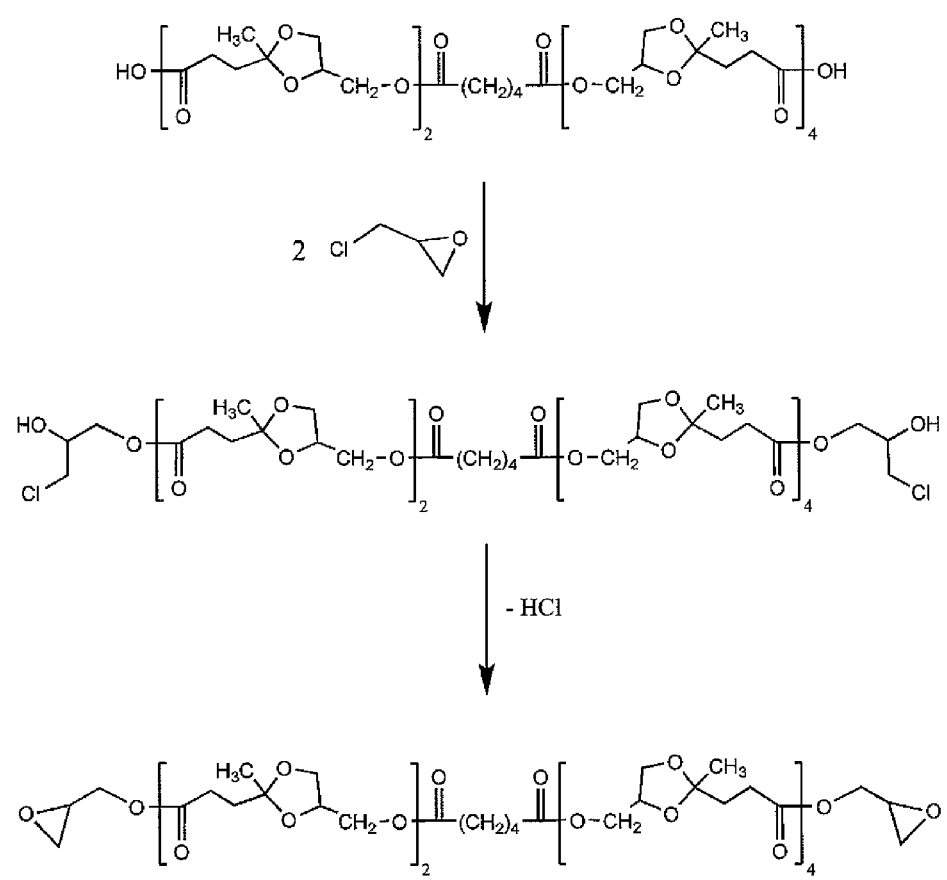
FIG. 3A shows a synthetic scheme for synthesis of a compound of the invention.

One example of such a reaction scheme for the reaction of epichlorohydrin with Precursor P2 wherein $R^2$ is —$(CH_2)_2$—, $R^3$ is —$CH_3$, $R^4$ is the residue of glycerol, $R^{11}$ is —$(CH_2)_4$—, β is 2, a first α is 2 and a second α is 4, is shown in FIG. 3A. In still other embodiments where $R^{12}$ of Precursor P2 is hydrogen and/or one or more carboxylic acid groups are present on $R^{11}$, carboxylate salts are formed using standard techniques; the salts are then reacted with an epihalohydrin, such as epichlorohydrin, to form the corresponding glycidyl compound III. In such embodiments, the techniques employed by, for example, Maerker et al., J. Org. Chem. 26, 2681-2688 (1961) are useful, among other techniques.

Figure 3B:
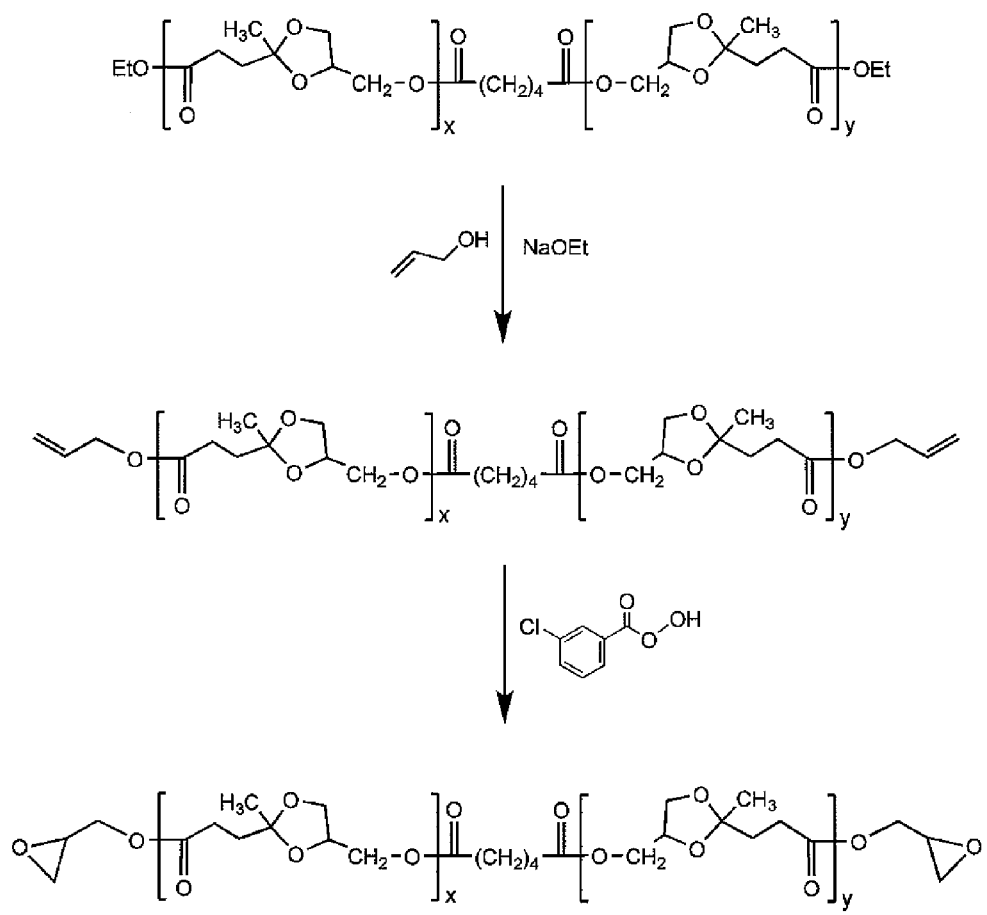
FIG. 3B shows an alternative synthetic scheme for the synthesis of a compound of the invention.

Another technique employed, in some embodiments, to provide glycidyl functionality to one or more Precursors P1 and P2 of the invention is to react an unsaturated site present on the molecule with a peroxide or another oxidizing agent. For example, Au, U.S. Pat. No. 5,036,154, discloses a method whereby an ethylenically unsaturated ester group, such as an allyl ester, is reacted with a peroxide, such as benzoic peroxide, or a peracid, such as m-chloroperoxybenzoic acid, in the presence of an alkali metal or alkaline earth metal salt of tungstic acid, phosphoric acid, and a phase transfer catalyst to give the epoxidized product of the unsaturated moiety. Such a technique is used, in embodiments, to form a glycidyl compound II or III of the invention from the corresponding allyl compound II or III, the allyl compounds II and III having been described above. An example of such a reaction is shown in FIG. 3B. Other techniques employed in the literature are similarly useful to obtain one or more epoxidized products of allyl compounds II and III of the invention. For example, esterification or transesterification of a Precursors P2 of the invention with an unsaturated fatty acid ester is followed, in embodiments, by reacting the unsaturated site with hydrogen peroxide, as is described by Du et al., *J. Am. Org. Chem. Soc.* 81(4) 477-480 (2004).

In a related reaction, the hydroxyl moieties of a Precursor P1 compound may be functionalized with isocyanate groups, then further reacted with a glycidyl alcohol to form oxiranyl compounds II. For example, in one such embodiment, a Precursor P1 having β of 2 and two hydroxyl moieties is reacted with two equivalents of a diisocyanate to form two urethane groups with terminal isocyanate moieties; in a subsequent reaction, the terminal isocyanates are reacted with glycidyl alcohol to give the corresponding oxiranyl compound II. Suitable diisocyanates useful in reactions with the hydroxyl groups of the Precursors P1 include, without limitation, those represented by formula OCN—Z—NCO and related compounds as are described above.

In embodiments, the oxiranyl compounds II and glycidyl compounds III are subsequently polymerized or grafted using standard techniques from the literature to form oxiranyl adducts IV and V, respectively. The reaction of oxirane groups, for example with amines, amides, or anhydrides, is widely known; of these, amines are the most commonly used compounds. A useful summary of compounds and mechanisms of polymerizing oxirane groups is found in Chanda, M. and Roy, S., eds., *Plastics Technology Handbook*, 4$^{th}$ ed., © 2007 Taylor & Francis Group, LLC, pp. 4-116 to 4-122. Any of the techniques employed or referenced therein are used, in various embodiments, to react the oxirane or glycidyl compounds II and III to form the corresponding linear, branched, or crosslinked polymeric adducts IV and V as well as grafted compounds and polymers IV and V Amines useful in various embodiments as a reagent to polymerize oxiranyl compounds II and glycidyl compounds III include diamines and higher polyamines. Suitable diamines and higher polyamines include hydrazine, ethane-1,2-diamine, 1,6-hexanediamine, but-2-ene-1,4-diamine, Metformin, butane-1,4-diamine, propane-1,2-diamine, piperazine, 2,2,4-trimethyl-1,6-hexanediamine, 2,4,4-trimethyl-1,6-hexanediamine, benzene-1,3-diamine, 2-methylbenzene-1,3-diamine, 4-chlorobenzene-1,3-diamine, methanediamine, 1,3,5-triazine-2,4,6-triamine, N-(2-aminoethyl)ethane-1,2-diamine, N-(6-aminohexyl)hexane-1,6-diamine, N,N'-bis(2-aminoethyl)ethane-1,2-diamine, N-[2-(3-aminopropylamino)ethyl]propane-1,3-diamine, 4-(3,4-diaminophenyl)benzene-1,2-diamine, spermine (N,N'-bis(3-aminopropyl)butane-1,4-diamine), diethylene triamine, dipropylene triamine, dihexylene triamine, 1,2,4-triazole-3,4,5-triamine, 2,4,5-triaminotoluene, melamine (1,3,5-triazine-2,4,6-triamine), benzene-1,3,5-triamine, triethylene tetramine, norspermine, N-[2-(3-aminopropylamino)ethyl]propane-1,3-diamine, 4-(3,4-diaminophenyl)benzene-1,2-diamine, a polyethyleneimine, a polyoxyalkyleneamine having two or more amine groups, such as those sold under the trade name JEFFAMINE®, (available from the Huntsman Corp. of Salt Lake City, Utah), or any diamine or higher amine compound such as those sold under the trade name ELASTAMINE® (available from the Huntsman Corporation).

Formulations with oxiranyl compounds II and glycidyl compounds III include, in various embodiments, an amine (such as in a two-part glue formulation), one or more additional oxiranyl compounds to copolymerize with the oxiranyl compounds II and glycidyl compounds III, a filler, a solvent, a polymer, a surfactant, a crosslinker, a UV stabilizer, a thermal stabilizer, an antioxidant, a colorant, a plasticizer, or a bleaching compound, or a combination thereof Additional "oxiranyl compounds" include compounds having two or more oxirane moieties that are capable of copolymerization with oxiranyl compounds II and glycidyl compounds III. Examples of suitable additional oxiranyl compounds include bisoxiranyl compounds such as 2-(oxiran-2-ylmethoxymethyl)oxirane (diglycidyl ether) 1,4-diglycidyloxybutane, bis(oxiran-2-ylmethyl) cyclohexane-1,2-dicarboxylate, 2-[6-(oxiran-2-yl)hexyl]oxirane, 2-[2-(oxiran-2-yl)ethyl]oxirane, 2-[2-[2-[2-(oxiran-2-ylmethoxy)ethoxy]ethoxy]ethoxymethyl]oxirane, 2-[[2,2-dimethyl-3-(oxiran-2-ylmethoxy)propoxy]methyl]oxirane (neopentyl glycol diglycidyl ether), bis(2,3-epoxypropyl)adipate, 2-[[4-[2-[4-(oxiran-2-ylmethoxy)phenyl]propan-2-yl]phenoxy]methyl]oxirane (diglycidyl adduct of Bisphenol A), 2-[2-(oxiran-2-yl)phenyl]oxirane, 2-[[3-(oxiran-2-ylmethoxy)phenoxy]methyl]oxirane, N,N-bis(oxiran-2-ylmethyl)aniline, 1,4-bis(oxiran-2-ylmethyl)piperazine, diglycidyl isophthalate, [dimethyl-[3-(oxiran-2-ylmethoxy)propyl]silyl]oxy-dimethyl-[3-(oxiran-2-ylmethoxy)propyl]silane, and the like as well as trisoxiranyl and higher polyoxiranyl compounds, such as 4-(oxiran-2-ylmethoxy)-N,N-bis(oxiran-2-ylmethyl)aniline and 2-[[3-(oxiran-2-ylmethoxy)-2,2-bis(oxiran-2-ylmethoxymethyl)propoxy]methyl]oxirane (pentaerythritol glycidyl ether).

In some embodiments, oxiranyl adducts IV and V are copolymers. Such adducts arise where, for example, the oxiranyl compounds II and glycidyl compounds III are copolymerized with one or more additional oxiranyl compounds. Copolymers are also formed where, for example, more than one diamine is employed in the polymerization of the oxiranyl compounds II and glycidyl compounds III. The properties and applications of copolymeric oxiranyl adducts IV and V, as well as the biomass content thereof, are not particularly limited. Applications of oxiranyl adducts IV and V, including copolymers, and grafted adducts IV and V, are numerous and broad in scope. Due to their high strength, variable crosslink density, and variable chemical starting materials, oxiranyl formulations, or epoxies, have found broad use in numerous applications. One of the most well known applications is in situ polymerization of oxiranyl compounds deliverable as a two-part "glue". Many of the most common applications are set forth in Chanda, M. and Roy, S., eds., *Plastics Technology Handbook*, 4th ed., © 2007 Taylor & Francis Group, LLC, pp. 2-80 to 2-81, 7-26, and 4-124 to 4-125. The oxiranyl adducts IV and V, formed by curing and/or grafting the glycidyl and oxiranyl compounds II and III optionally in the presence of one or more additional oxiranyl compounds are, in various embodiments, useful in one or more of these applications.

The oxiranyl compounds II and III and oxiranyl adducts IV and V of the invention are synthesized, in preferred embodiments, from biomass-based feedstocks. For example, the glycerol and 1,1,1-trimethylolpropane ketals of levulinic and pyruvic acid, and esters thereof, that form the Precursors P1 and P2 are derivable or potentially derivable from biomass sources and do not require the use of petroleum based feedstocks. Thus, the current invention enables the synthesis of a biomass based set of oxiranyl compounds II and III and polymers, crosslinkers, and grafted materials made from them; oxiranyl materials are well known to be industrially useful in a wide variety of applications. In embodiments, at least 20% by weight of the oxiranyl compounds II and III and oxiranyl adducts IV and V are biomass based. In other embodiments, between about 20% and 90% by weight of the oxiranyl compounds II and III and oxiranyl adducts IV and V are biomass based. In other embodiments, between about 40% and 75% by weight of the oxiranyl compounds II and III and oxiranyl adducts IV and V are biomass based. FIG. 11 shows a list of representative compounds of the invention and their biomass content by weight. Additionally, the oxiranyl compounds II and III and adducts thereof IV and V of the invention are, in some embodiments, biodegradable. Biodegradable oxiranyl compounds are useful for one or more applications, for example, in biodegradable adhesive formulations. In various embodiments, the oxiranyl compounds II and III and adducts thereof IV and V of the invention advantageously supply the desirable properties of known oxiranyl monomers, polymers, and grafted materials and additionally supply biodegradability thereof. Additionally, the oxiranyl compounds II and III and adducts thereof IV and V are, in some embodiments, capable of selective hydrolytic degradation at the ketal linkage. Ketal moieties undergo rapid and quantitative hydrolytic degradation in the presence of strong mineral acid and water using mild temperatures and pressures to produce a ketone and an alcohol. This selective degradation is accomplished, in embodiments, in the presence of other functional groups such as esters, amides, alcohols, allyl groups, acrylates, carbonates, and ethers that remain intact. The selective degradation of the ketal linkage in the oxiranyl adducts IV and V is employed in some embodiments to provide additional functionality to the polymer, i.e. ketone or hydroxyl groups for further grafting reactions or compatibility and/or desired differences in hydrophilicity. Also, this chemical degradation is advantageous in some embodiments for lithography applications of the oxiranyl adducts IV and V, wherein a photo-acid generator (usually a strong acid) selectively cleaves the labile ketal linkage of the oxiranyl adducts IV and V to generate reactive hydroxyl groups or ketone groups for various applications. An additional advantage of selective degradation is that it enables, in embodiments, the breakdown of high molecular weight adducts to lower molecular weight species for ease of disposal, recyclability, and/or degradation by erosion or thermal means.

The polycarbonates, acrylate and alkacrylate adducts, allyl adducts, and oxiranyl and glycidyl adducts IV and V are useful in a wide variety of industrially useful and significant applications. Various adducts IV and V of the invention are, in embodiments, used in blends, optionally obtained by reactive extrusion. Blends include those of various polymers, for example various species of the polycarbonates, acrylic polymers, allyl polymers, and oxiranyl polymers of the invention as well as blends with such polymers as aliphatic/aromatic copolyesters, as for example polybutylene terephthalate adipate (PBTA), polybutylene terephthalate succinate (PBTS), and polybutylene terephthalate glutarate (PBTG); biodegradable polyesters such as polylactic acid, poly-ε-caprolactone, polyhydroxybutyrates such as poly-3-hydroxybutyrates, poly-4-hydroxybutyrates and polyhydroxybutyrate-valerate, polyhydroxybutyrate-propanoate, polyhydroxybutyrate-hexanoate, polyhydroxybutyrate-decanoate, polyhydroxybutyrate-dodecanoate, polyhydroxy-butyrate-hexadecanoate, polyhydroxybutyrate-octadecanoate, and polyalkylene succinates and their copolymers with adipic acid, lactic acid or lactide and caprolactone and their combinations, and the like; polystyrene and copolymers thereof; polyurethanes; polycarbonates; polyamides such as Nylon 6 and Nylon 6,6; polyolefins such as polyethylene, polypropylene, and copolymers thereof; or any other industrially useful polymeric compounds. Blends also include, in some embodiments, composites with gelatinized, destructed and/or complexed starch, natural starch, flours, and other materials of natural, vegetable or inorganic origin. The adducts IV and V of the invention are, in some embodiments, blended with polymers of natural origin, such as starch, cellulose, chitosan, alginates, natural rubbers or natural fibers (such as for example jute, kenaf, hemp). The starches and celluloses can be modified, such as starch or cellulose esters with a degree of substitution of between 0.2 and 2.5, hydroxypropylated starches, or modified starches with fatty chains, among others.

The adducts IV and V, and blends of thereof, possess properties and values of viscosity that render them suitable for use, by appropriately adjusting the molecular weight, in numerous practical applications, such as films, injection-molded products, extrusion coated products, fibers, foams, thermoformed products, extruded profiles and sheets, extrusion blow molding, injection blow molding, rotomolding, stretch blow molding and the like.

In the case of films, production technologies like film blowing, casting, and coextrusion can be used. Moreover such films can be subject to monoaxial or biaxial orientation in line or after film production. It is also possible that the stretching is obtained in presence of an highly filled material with inorganic fillers. In such a case, the stretching can generate micropores and the so obtained film can be suitable for hygiene applications. The adducts IV and V are suitable for the production of films. A "film" is defined, for the purposes of the invention, as a sheet type material that is flexible to e.g. bending and is between about 1 μm to 5 mm thick. Films employing the adducts IV and V are, in embodiments, one-directional or two-directional, single layer or multilayer, and employ an adduct IV or V as a single component or in a blend with other materials, as described above. The films are useful for various applications including agricultural mulching films; printable films for graphics or text; cling films (extensible films) for foodstuffs, films for bales in the agricultural sector and for wrapping of refuse; shrink films such as for example for pallets, mineral water, six pack rings, and so on; bags and liners such as for collection of refuse, holding foodstuffs, gathering mowed grass and yard waste, and the like; thermoformed single-layer and multilayer packaging for foodstuffs, such as for example containers for milk, yogurt, meat, beverages, etc.; and in multilayer laminates with layers of paper, plastic materials, aluminum, metalized films for a wide variety of applications.

The adducts IV and V are also useful for coatings that form a layer on top of a film, an article, and the like. Coatings of the invention are applied, in embodiments, by extrusion coating, die coating, slot coating, brush coating, spray coating, or any other generally known technique employed in the coating industry. Coatings employing adducts IV and V are useful as protective coatings, paint components, adhesives or glues, barrier layers, and the like. The coatings of the invention are applied, in embodiments, with or without additional solvent(s), such as coalescing solvents, and with our without additives such as tougheners, plasticizers, surfactants, fillers, UV blocking agents, thermal stabilizers, antioxidants, antibacterial agents, colorants, fillers, and the like. The coatings of the invention are, in some embodiments, crosslinked after application.

Adducts IV and V are also useful in forming articles. An "article", as defined for the purposes of the invention, includes objects that are be rigid or flexible; that exist as standalone objects or as part of an assembly or laminate; and that include adducts IV or a blend thereof with one or more additional materials. Some examples of useful articles that include adducts IV are punnets for foodstuffs, I-beams for construction, casings for e.g. pens, computer screens, and the like; parts for automobile construction, table tops, and the like; decorative items such as lamp parts, jewelry, vases, architectural features, and the like; children's toys; drink bottles; and many other articles. The invention is not particularly limited in terms of what articles may be formed employing the adducts IV and V of the invention.

Articles that can be formed include foamed articles. Foaming techniques that are generally known in the industry are used, in embodiments, to form foamed articles from the various adducts IV and V. Foamed articles include both rigid and flexible foams. Some examples of useful foamed materials include cushions for automobile seats, interior or exterior furniture, and the like; foamed or foamable beads for the production of pieces formed by sintering; foamed blocks made up of pre-foamed particles; foamed sheets, thermoformed foamed sheets, and containers obtained therefrom for the packaging of foodstuffs.

Articles also include fibrous articles. Examples of fibrous articles include standard scale fibers, microfibers, nanofibers, and composite fibers. Composite fibers have, in embodiments, a core constituted by a rigid polymer such as PLA, PET, PTT, etc. and an external shell made with one or more adducts IV; other composite fibers have various section configurations, e.g. from round to multilobed. Fibers also include flaked fibers, woven and non-woven fabrics or spun-bonded or thermobonded fabrics for the sanitary sector, the hygiene sector, the agricultural sector, georemediation, landscaping and the clothing sector. Fibrous articles also include fiber-reinforced composites, which include fibers, resins, and other components to form part of high strength and rigidity. In such embodiments, the adducts IV and V make up all or a portion of the resin material used to impregnate the fibers. Carbon fiber is one example of a fiber that is useful in a fiber reinforced composite of the invention. In embodiments, compounds II and III are used to impregnate the fiber, then polymerization and optionally grafted is carried out in situ to form the composite adducts IV and V, respectively.

The allyl, oxiranyl and glycidyl compounds II and III are also useful, in one or more embodiments, as reactive diluents in a wide variety of formulations. Reactive diluents are compounds that are used, in some embodiments, to replace organic solvents in conventional high-VOC (volatile organic compound) coatings. Reactive diluents function like solvents in adjusting coating viscosity for various applications. However, rather than evaporating like conventional solvents, reactive diluents participate in a chemical reaction with the coating components during the curing process, and become incorporated into the cured coating. As noted above, Precursors P2 include several species known to be effective plasticizers in poly(vinyl chloride) formulations. In embodiments, providing reactive endgroups onto these or other Precursor species P1 and P2 enables the compounds to be used as reactive diluents in a formulation. Many coating applications feature reactive diluents to facilitate coating viscosity, leveling, and the like, followed by reactions to incorporate the diluents into the polymeric network subsequently formed.

The following Examples further elucidate and describe the compounds of the invention without limiting the scope thereof.

EXPERIMENTAL SECTION

Example 1

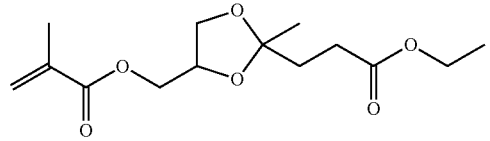 [SMILES: C=C(C)C(=O)OCC1COC(C)(CCC(=O)OCC)O1]

A 3-neck round bottom flask (rbf) was charged with 54.58 gm (0.25 moles) of ethyl 4-(2-hydroxymethyl-1,4-dioxolan-5-yl) pentanoate ("EtLGK", made according to the procedure of PCT Application No. WO 2009/048874). The rbf was equipped with 2 rubber septa, a thermocouple fitted using an adapter and Teflon coated magnetic spindle for stirring. Nitrogen purge was started in the rbf and the stirrer was set at 400 rpm. Then 40.44 mL (0.5 moles) of pyridine (obtained from the Sigma-Aldrich Company of St. Louis, Mo.) was carefully added to the rbf using a 60 mL syringe. The rbf was immersed in an ice bath to cool the reaction mixture. When the temperature of the mixture reached 0° C. (0.5° C. actual temperature), 36.64 mL (0.375 moles) of methacryloyl chloride (obtained from the Fluka Chemical Corporation of Milwaukee, Wis.) was slowly added to the rbf using a 60 mL syringe. The reaction temperature was maintained below 25° C. by controlling the rate of addition of methacryloyl chloride. About 20 minutes after completing the addition, the ice bath was removed and the reaction mixture was allowed to warm to room temperature. The reaction mixture was stirred at ambient temperature for another 3 hours. A white precipitate was observed to form during the 3 hours.

The white precipitate was dissolved in a mixture of 50 mL water and 50 mL 0.1 N NaOH. The aqueous phase was then extracted with $CH_2Cl_2$ (3×100 mL) and the resulting organic phase was washed with a saturated solution of NaCl (1×50 mL) and dried using $Na_2SO_4$. Then 7.0 mg ($3.39×10^{-5}$ moles) of 2,6-di-tert-butylphenol (obtained from the Sigma-Aldrich Company of St. Louis, Mo.) was added to the solution before removing the $CH_2Cl_2$ and pyridine by rotary evaporation. The final product was pale yellow liquid, which was analyzed by GC-MS and ¹HNMR. GC-MS data: 96.7% of the methacrylyl adduct of EtLGK, 3.3% crotonyl chloride.

Example 2

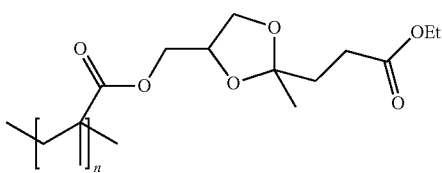

Figure 4:
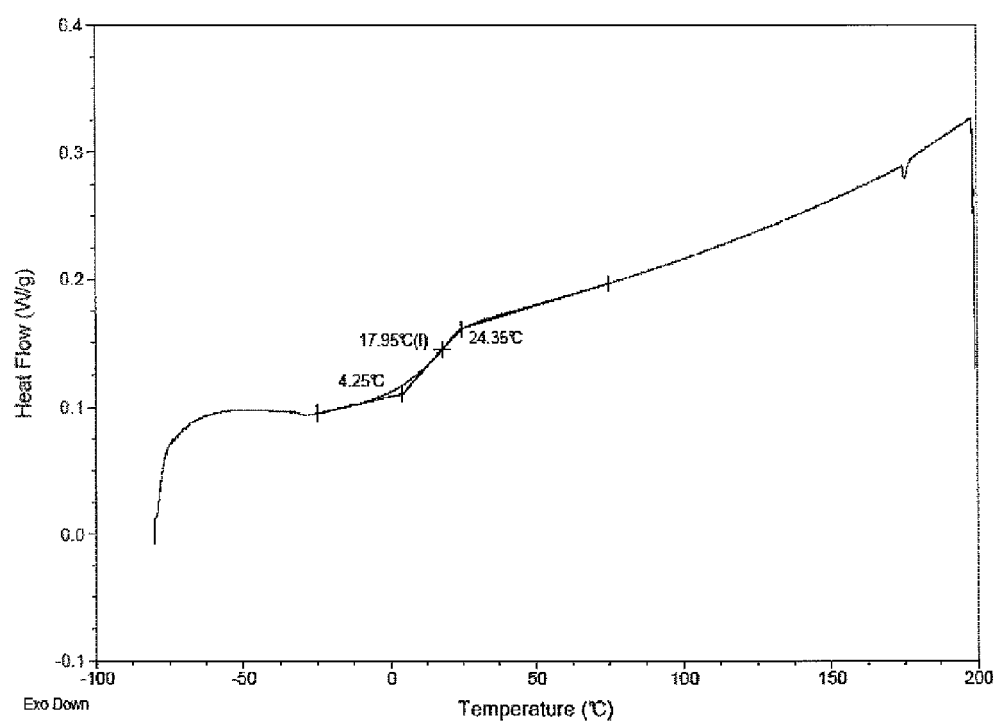
FIG. 4 shows a differential scanning calorimetry plot for a compound of the invention.

A 20 mL scintillation vial was charged with 1.0 gm of the final methacrylate product of Example 1. Then 50 mg (5 wt %) AIBN (obtained from the Sigma-Aldrich Company of St. Louis, Mo.) was added. The vial was capped with a rubber septum. The reaction mixture was deoxygenated by alternately pulling vacuum and back filling with nitrogen three times. The vial was placed in an oil bath heated to 70° C. The vial remained immersed in the oil bath for about 2 hours, then was removed and allowed to cool to ambient temperature. Then 10 mL of $CH_2Cl_2$ was added to the polymer and the contents of the vial were stirred overnight using a Teflon coated magnetic spindle at 220 rpm. An undissolved solid product was filtered from the contents of the vial and washed with $CH_2Cl_2$ (2×10 mL). The washed product was dried overnight in a vacuum oven set to 120° C. at a pressure of about 300 millitorr. The white transparent product turned slightly yellow after drying in the oven. The product was analyzed by DSC and was found to have a glass transition temperature ($T_g$) of 17.95° C. The DSC is shown in FIG. 4.

Example 3

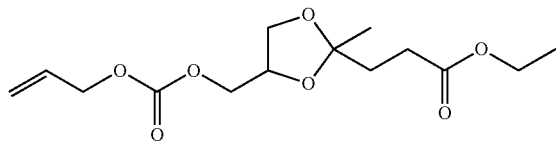 [SMILES: C=CCOC(=O)OCC1COC(C)(CCC(=O)OCC)O1]

Figure 5:
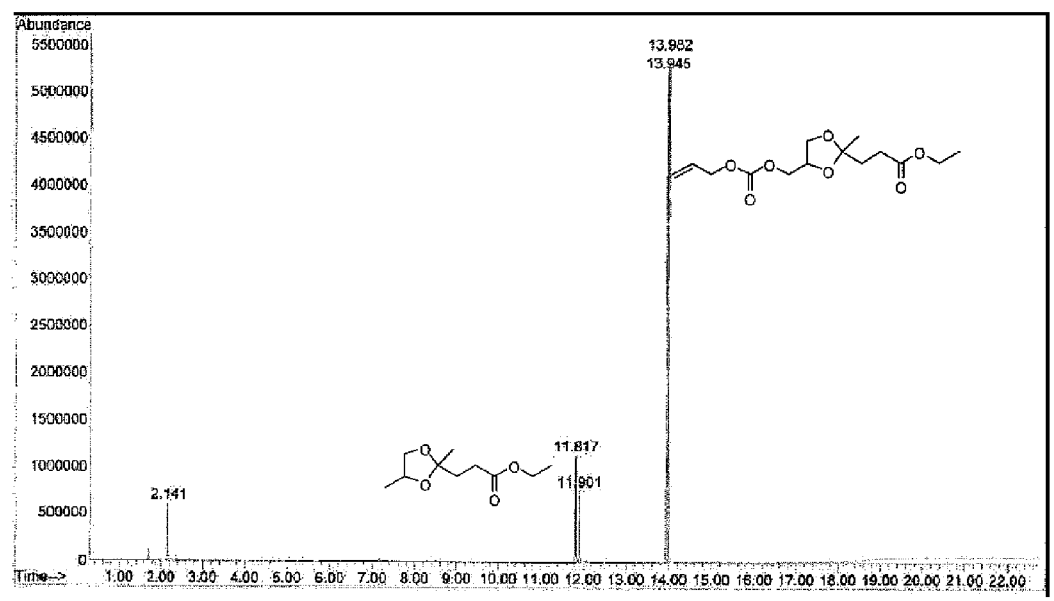
FIG. 5 shows a gas chromatograph for a compound of the invention.

A 3-neck roundbottom flask (rbf) was charged with 43.66 gm (0.20 moles) EtLGK. The rbf was equipped with 2 rubber septa and a thermocouple fitted using an adapter. Nitrogen purge was started and was maintained throughout the course of the reaction. Then 32.35 mL (0.4 moles) of pyridine (obtained from the Sigma-Aldrich Company of St. Louis, Mo.) was added using a 60 mL syringe. The rbf was immersed in an ice bath to cool the reaction mixture to 0° C. Then 31.86 mL (0.3 moles) of allylchloroformate (obtained from Acros Organics of Geel, Belgium) was slowly added to the reaction mixture using a 60 mL syringe. The temperature of the reaction mixture was maintained below 25° C. by controlling the rate of addition of the allylchloroformate. After the addition was completed, the contents of the flask were stirred in the ice bath for an additional 20 minutes. Then the reaction mixture was then allowed to warm to ambient temperature and stirred for another 3 hours. A white precipitated was observed in the rbf; the precipitate was filtered from the remainder of the flask contents using a Millipore filter (0.45 μm HNWP, Millipore, Ireland). The liquid contents were washed with 20 mL of 0.1 N NaOH, followed by 20 mL water, then and 20 mL of saturated NaCl solution. The washed product was dried with $Na_2SO_4$ and filtered. The excess pyridine was removed using rotary evaporator. The final product was a pale yellow liquid. The final product was analyzed by GC-MS, which showed 85% of the allylcarbonate adduct of EtLGK (rt=13.95-13.98 min) The GC-MS of the final product is shown in FIG. 5.

Example 4

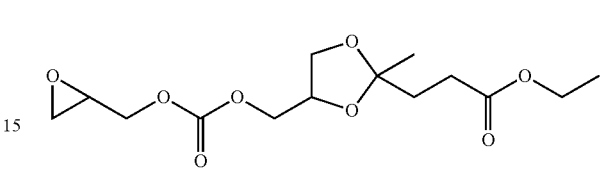

Figure 6:
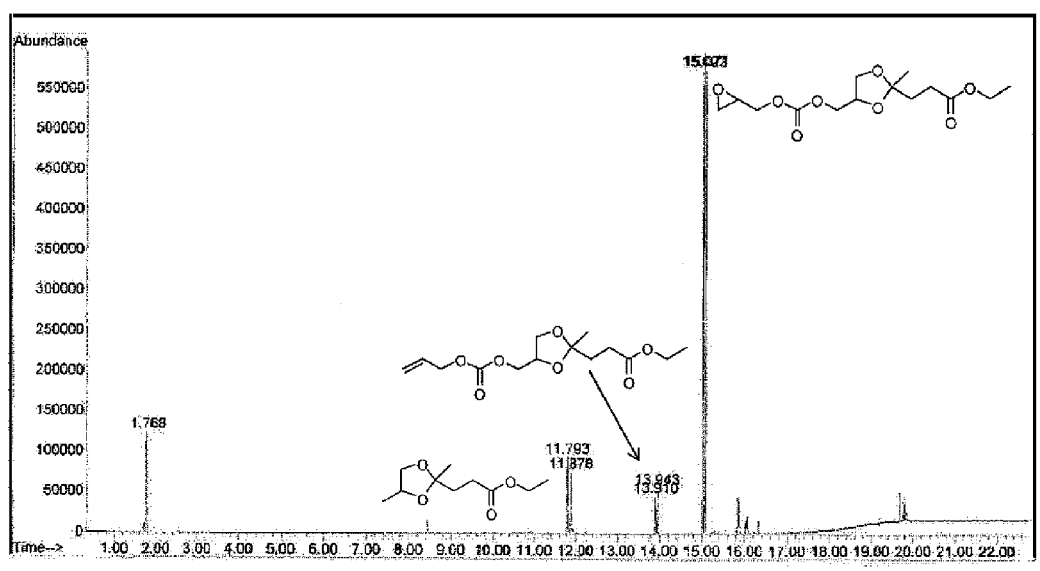
FIG. 6 shows a gas chromatograph for a compound of the invention.

A single-neck round bottom flask (rbf) was charged with 5.0 gm (0.0165 moles) of the final product of Example 3 and 30.0 mL of $CHCl_3$ (obtained from Fisher Scientific of Waltham, Mass.), followed by addition of 3.8 gm (0.0187 moles) 85% m-chloroperoxybenzoic acid (obtained from the Sigma-Aldrich Company of St. Louis, Mo.). The rbf was equipped with a condenser and placed in an oil bath set at 63° C. The contents of the flask were refluxed for about 8.5 hrs. Then another 0.65 g (0.0032 moles) of m-chloroperoxybenzoic acid was added to the flask and the contents of the flask were refluxed for about 16 hours. A white precipitated formed after the reaction was cooled to room temperature. The precipitate was filtered using Millipore filter and washed with 30 mL $CHCl_3$. The liquid contents of the flask were washed with 1 N NaOH (2×10 mL), followed by water (10 mL) and sat. NaCl (10 mL), then dried with $Na_2SO_4$ and filtered. The $CHCl_3$ was removed using rotovap. The final product was a clear liquid that was analyzed by GC-MS. GC-MS data showed a yield of 73% of the oxiranylcarbonate adduct of EtLGK. The GC-MS of the final product is shown in FIG. 6.

Example 5

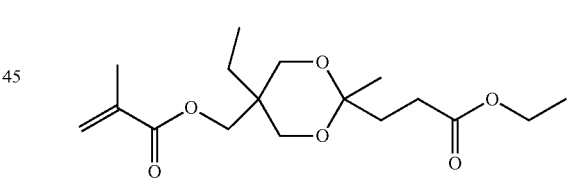

A 2 liter, single neck round bottom flask was equipped with a stir bar and charged with 873.90 g (6.07 mol) of ethyl levulinate (obtained from Langfang Triple Well Chemicals Company, Ltd. Of Langfang City, HeBei, China), 407.5 g (3.04 mol) 1,1,1-trimethylolpropane (obtained from the Sigma-Aldrich Company of St. Louis, Mo.) and 16.2 μl (0.304 mmol) of 98% sulfuric acid (obtained from the Sigma-Aldrich Company of St. Louis, Mo.). The flask was placed on a rotary evaporator with an oil bath temperature of 75° C. and was subjected to a vacuum of between 10 and 20 torr. The flask was rotated on the rotary evaporator for about 2.5 hours and then the temperature of the oil bath was raised to 90° C. This temperature was maintained for about 1 hour and then the temperature was increased, again, to 100° C. and maintained for 1 hour 45 minutes. The temperature was then raised again to 110° C. and was maintained at that temperature for about 10 minutes. For each step in temperature, the contents of the reaction flask were observed to bubble and a liquid was observed to be condensing on the rotary evaporator. At the point that the bubbling stopped and liquid was observed to stop collecting on the condenser, the next step in temperature was taken.

After the oil bath was maintained at 110° C. for about 10 minutes the flask was removed from the rotary evaporator and the contents of the flask allowed to cool to room temperature. A sample of the crude reaction product was removed from the flask and analyzed by GC. The analysis showed that the contents consisted of about 54.5% of the trimethylolpropane ketal of ethyl levulinate ("EtLTMPK"), about 38.7% ethyl levulinate, about 4.9% trimethylolpropane, and approximately 1% of unknown side reaction products.

Then 654.2 g of the crude reaction product was placed in a 1 liter round bottom flask. Teflon boiling chips and a stir bar were added to the flask. The flask was equipped with a fractionation column, condenser, and vacuum/nitrogen inlet. A vacuum was applied to the flask, with stirring, until the pressure reached about 9 torr. A heating mantle was applied to the flask and the heat setting was set to 7.5 on a scale of 10. After about 1 hour the temperature in the distillation column head was observed to reach 74° C. Over the next 20 minutes the head temperature was fluctuating between 74 and 85° C. and a liquid was observed to condense in the condensation column. Over the following 15 minutes the temperature in the distillation head was observed to slowly rise to 165° C. and a small fraction of the liquid distilling at 165° C. was collected. Then the vacuum was released and the contents of the reaction flask were allowed to cool to room temperature; a sample of the stripped crude reaction product was removed for GC analysis. The GC results showed a yield of 89.7% EtLTMPK.

A 1 liter round bottom flask was charged with 401.90 g of the stripped crude reaction product and the flask placed on a rotary evaporator with a bump flask inserted between the 1 liter flask and the condenser column of the rotary evaporator. The flask and bump flask were rotated in an oil bath set to 180° C. while a vacuum of about 4-8 torr was applied. A clear liquid was observed to collect in the bump flask and periodically the vacuum on the rotary evaporator was released in order to empty the contents of the bump flask into a clean, dry storage vessel. In this way the entire batch of crude stripped reaction product was distilled and combined.

The total yield of distilled, combined EtLTMPK was 69.9 mol % based on theoretical. A sample of the distilled, combined EtLTMPK was subjected to GC and TGA analysis. The GC showed 96.8% EtLTMPK.

A 3-neck roundbottom flask was charged with 26.06 gm (0.1 moles) of the distilled, combined EtLTMPK and the flask was equipped with 2 rubber septa and a thermocouple fitted using an adapter. Nitrogen purge was started and was maintained throughout the course of the reaction. Then 22.0 mL (0.2 moles) of pyridine (obtained from the Sigma-Aldrich Company of St. Louis, Mo.) was added using a 30 mL syringe. The flask was immersed in an ice bath. Upon reaching a temperature of about 0° C. (0.5° C.), 15.0 mL (0.15 moles) of methacryloyl chloride (obtained from the Fluka Chemical Corporation of Milwaukee, Wis.) was slowly added to the flask using an addition funnel The reaction temperature was maintained below 25° C. by controlling the rate of addition of the methacryloyl chloride. After completion of the addition, the flask was stirred in the ice bath for about 20 minutes, then the flask was removed from the ice bath and allowed to warm to ambient temperature. The reaction mixture was stirred at ambient temperature for another 3 hours. At the end of the reaction period, a white precipitated was observed. The precipitate was dissolved in 10 mL water and 10 mL 0.1 N NaOH. The aqueous phase was extracted using $CH_2Cl_2$ (3×100 mL) and the resulting organic phase was washed with once with 10 mL of a saturated NaCl solution, then dried using $Na_2SO_4$ followed by filtration. Then 4.6 mg ($2.22×10^{-5}$ moles) of 2,6-di-tert-butylphenol (obtained from the Sigma-Aldrich Company of St. Louis, Mo.) was added to the solution before removing the $CH_2Cl_2$ and pyridine by rotary evaporation to yield the final product. The final product was pale yellow liquid that was analyzed by GC-MS, which showed a yield of 92.4% of the methacryloyl adduct of EtLTMPK.

Example 6

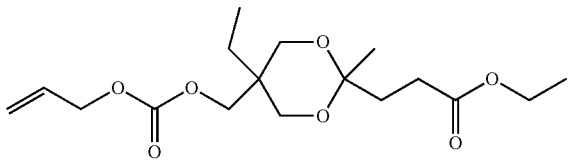 [SMILES: C=CCOC(=O)OCC1(CC)COC(C)(CCC(=O)OCC)OC1]

A 3-neck roundbottom flask (rbf) was charged with 26.14 gm (0.10 moles) EtLTMPK (intermediate product of Example 5) and the flask was equipped with 2 rubber septa and a thermocouple fitted using an adapter. Nitrogen purge was started and was maintained throughout the course of the reaction. Then 16.0 mL (0.2 moles) pyridine (obtained from the Sigma-Aldrich Company of St. Louis, Mo.) was added using a 20 mL syringe. The rbf was immersed in an ice bath to cool the reaction mixture to 0° C. (0.5° C.). Then 11.0 mL (0.15 moles) of allylchloroformate (obtained from Acros Organics of Geel, Belgium) was slowly added to the reaction mixture using an addition funnel The reaction temperature was maintained below 25° C. by controlling the rate of addition of the allylchloroformate. After completion of the addition the contents of the flask were stirred in the ice bath for an additional 20 minutes, then the flask was removed from the ice bath and allowed to warm to ambient temperature. The contents of the flask were allowed to stir for an additional 3 hours. A white precipitated was observed to form during the reaction. The precipitate was filtered from the liquid contents of the flask using a Millipore filter. The filtered reaction mixture was washed with 10 mL of 0.1 N NaOH, followed by 10 mL water and 10 mL saturated NaCl solution, followed by drying with $Na_2SO_4$ and filtration. The excess pyridine was removed using a rotary evaporator to give the final product. The final product was a pale yellow liquid which was analyzed by GC-MS and $^1H$ NMR. The GC-MS data showed 76.9% of the allylcarbonate adduct of EtLTMPK.

Example 7

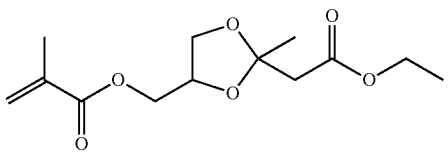 [SMILES: C=C(C)C(=O)OCC1COC(C)(CC(=O)OCC)O1]

A 500 mL 3-neck round bottom flask was charged with 186.08 g (2.00 mol) glycerol (obtained from Acros Organics of Geel, Belgium) and 1045.88 g (8.04 mol) ethyl acetoacetate (obtained from the Sigma-Aldrich Company of St. Louis, Mo.). The contents of the flask were observed to consist of a heterogeneous mixture of two liquid phases. The flask was equipped with an overhead mechanical stirrer, a Dean-Stark separator with an overhead condenser, and a thermocouple. The contents of the flask were blanketed with a nitrogen stream and heated to 110° C. while stirring. Once the contents were at 90° C., 21.3 µL ($2.0 \times 10^{-4}$ moles) of concentrated sulfuric acid (obtained from the Sigma-Aldrich Company of St. Louis, Mo.) was added into the flask below the surface of the contents by pipette. The contents of the flask began to bubble. The initial pressure in the flask was set to 300 Torr, and pressure was then ramped from 300 Torr to about 30 Torr over about 7 min. The contents of the flask were stirred for an additional 60 min at 25-30 Torr. During this time, a distillate was collected in the Dean Stark separator. The distillate was observed to separate as it cooled. A sample of the reaction mixture was removed for GC-MS analysis. The GC trace showed no evidence of glycerol. Only excess ethyl acetoacetate and the ethyl acetoacetate-glycerol ketal (EtAGK) were observed.

The EtAGK reaction product was poured into a beaker and neutralized by adding about 109 g (10 wgt %) of basic alumina (obtained from the Sigma-Aldrich Company of St. Louis, Mo.) and stirring the mixture for about 30 minutes at room temperature. The solids were filtered from the mixture using a fritted glass filter, fine grade. The liquids were vacuum distilled at between about 35 and 67 Torr using a 1 liter flask, fractionation column, condenser, and a cow with 3 catch flasks. A first liquid was observed to distil at about 95° C., and this was collected and analyzed by GC-MS and determined to be 100% ethyl acetoacetate. A second liquid was observed to distil at about 165° C. A very small amount of residual material was left in the distillation flask at the end of the distillation. In the catch flask for the second liquid, both liquid and an appreciable amount of a crystalline solid were observed. GC-MS showed that the second liquid was 99% EtAGK.

A 3-neck roundbottom flask (rbf) was charged with 30.62 gm (0.15 moles) EtAGK from and the flask was equipped with 2 rubber septa and a thermocouple fitted using an adapter. Nitrogen purge was started and was maintained throughout the course of the reaction. Then 41.81 mL (0.3 moles) of triethylamine (obtained from the Sigma-Aldrich Company of St. Louis, Mo.) was added using a 20 mL syringe. The rbf was immersed in an ice bath to cool the reaction mixture to 0° C. (0.5° C.). Then 22.0 mL (0.225 moles) of methacryloyl chloride (obtained from the Fluka Chemical Corporation of Milwaukee, Wis.) was slowly added to the reaction mixture using an addition funnel The reaction temperature was maintained below 25° C. by controlling the rate of addition. After completion of the addition the contents of the flask were stirred in the ice bath for an additional 20 minutes, then the flask was removed from the ice bath and allowed to warm to ambient temperature. The contents of the flask were allowed to stir for an additional 3 hours. A white precipitated was observed to form during the reaction. The precipitate was dissolved in 10 mL water and 10 mL 0.1 N NaOH. The aqueous phase was extracted with $CH_2Cl_2$ (3×50 mL) and the resulting organic phase was washed with 10 mL of a saturated NaCl solution and dried using $Na_2SO_4$, followed by filtration. Then 6.4 mg ($3.1 \times 10^{-5}$ moles) of 2,6-di-tert-butylphenol (obtained from the Sigma-Aldrich Company of St. Louis, Mo.) was added to the solution before removing the $CH_2Cl_2$ and $Et_3N$ by rotary evaporation to yield a final product. The final product was pale yellow liquid that was analyzed by GC-MS and $^1$H NMR. GC-MS data showed 93.5% of the methacryloyl adduct of EtAGK.

Example 8

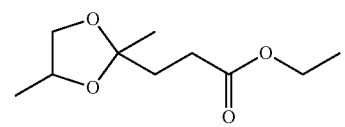

A reactor with a 15 L jacketed glass kettle was equipped with mechanical agitator, partial condenser attached to a circulating adjustable temperature chiller, a second condenser between the partial condenser and the receiving flask, and 1 L receiving flask. The condensers were both equipped with circulation baths with temperature controllers. The kettle was charged with 2.35 kg (16.31 moles) ethyl levulinate (obtained from the Langfang Triple Well Chemicals Company, Ltd. of Langfang City, HeBei, China) and 2.50 kg (32.85 moles) 1,2-propanediol (obtained from the Brenntag North America, Inc. of Reading, Pa.). The agitator speed was set to 50 rpm, the temperature of the partial condenser was set to 80° C., the temperature of the second condenser was set to 7° C., and the kettle temperature was set to 110° C. The pressure in the reactor was reduced gradually to a target pressure of 10-15 Torr. A liquid was observed to collect in the receiver. After about 1 hour at the target pressure and kettle temperature, the receiver was replaced with a fresh 1 L receiving flask. The partial condenser temperature was set to 112° C. and the kettle temperature was set to 170° C.; these settings were selected to allow excess propanediol and any unreacted ethyl levulinate to distill through the partial condenser and over to the second condenser, while the desired reaction product, the propanediol ketal of ethyl levulinate, was returned to the kettle by condensation in the partial condenser. The pressure in the reactor was adjusted to 10-15 Torr. When liquid stopped condensing in the receiver, a 5 L collection flask was attached to the reactor and the remainder of the liquid in the reactor kettle was distilled as a crude distillate by setting the partial condenser temperature to 110° C., kettle temperature to 170° C., and adjusting pressure to 10-15 Torr. The distillation was stopped before the reactor kettle was dry.

The crude distillate was analyzed by GC-FID and was determined to be about 33.37% propylene glycol, 66.48% of the 1,2-propanediol ketal of ethyl levulinate ("EtLPK"), and 0.15% ethyl levulinate. About 1 L of the crude distillate EtLPK was transferred to a 2 L separatory funnel The mixture was washed 2 times with 500 mL of brine solution and once with 500 mL of deionized water. The organic layer was dried with magnesium sulfate, filtered and analyzed for purity. Analysis of the washed and dried EtLPK product by GC-FID (calibrated to 100 ppm 1,2-propanediol) revealed no detectible propanediol and 0.14% ethyl levulinate.

Example 9

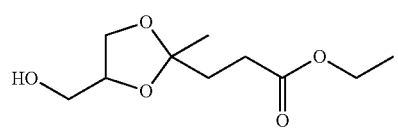

The reaction to form the glycerol ketal of ethyl levulinate ("EtLGK") was carried out according to the procedure of WO 2009/048874, Example 3, except that ethyl levulinate was obtained from the Langfang Triple Well Chemicals Company, Ltd. of Langfang City, HeBei, China and was not treated in any way prior to use; and glycerol was obtained from Cargill Inc. of Minnetonka, Minn. After synthesis was complete, EtLGK was purified by distillation of ethyl levulinate from of the crude reaction mixture at 5 Torr and 70-75° C. Subsequently, the EtLGK product was distilled from the crude reaction mixture at 5 Torr and 150-155° C. The final EtLGK product was determined to be 98.2% pure by GC-FID.

Example 10

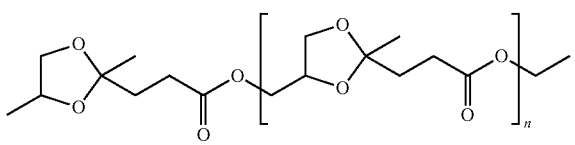

A 250 mL 3-neck round bottom flask was charged with 32.8 g (0.15 mol) EtLGK (synthesized according to the method of Example 9) and 91.0 g (0.45 mol) EtLPK (synthesized according to the method of Example 8). The flask was equipped with a mechanical stirrer, thermocouple, a Dean-Stark apparatus with condenser, and an inlet and outlet for nitrogen. The contents of the flask were stirred under a vacuum of about 6 torr and heated to 110° C. using a heating mantle. The flask was back-filled with nitrogen, a sample was taken from the flask, and the water content in the flask was measured to be 33 ppm by Karl Fischer titration. Then 9.7 μL of a titanium tetra-isopropoxide (obtained from the Sigma-Aldrich Company of St. Louis, Mo.) was added into the flask. Nitrogen purge was maintained and the contents of the flask were heated to 230° C. using a heating mantle. During the reaction, a liquid was observed to collect in the Dean-Stark trap. After a maintaining the temperature of 230° C. for about 2 hours the reaction mixture was cooled to 110° C., and distillation of a second liquid was accomplished using reduced pressure of about 4 Torr. The reaction mixture was allowed to cool to ambient temperature when no further distillate was collected.

After establishing atmospheric pressure in the flask, a sample was removed and analyzed by GPC. The composition as measured by GPC was about 48.6% of the 1:1 adduct of EtLGK:EtLPK, about 26.8% of the 2:1 adduct of EtLGK:EtLPK, about 12.2% of the 3:1 adduct of EtLGK:EtLPK, about 8.2% of the 4:1 adduct of EtLGK:EtLPK, and about 4.3% total of the starting materials EtLGK and EtLPK.

Example 11

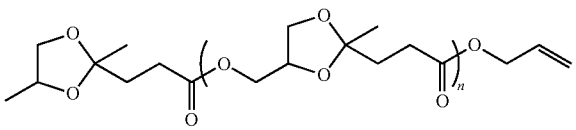

A 3-neck round bottom flask (rbf) was charged with 51.04 gm (0.1 moles) of the LPK-LGK adduct mixture of Example 10. The rbf was equipped with a thermocouple fitted using an adapter, a Dean-Stark fitted with a condenser, an adapter for nitrogen purge and Teflon coated magnetic spindle for stirring. Nitrogen purge was started in the rbf and the stirrer was set at 300 rpm. Then 10.2 mL (0.15 moles) of allyl alcohol (obtained from the Sigma-Aldrich Company of St. Louis, Mo.) was carefully added to the rbf using a 10.0 mL syringe. The rbf was heated using a heating mantle connected to a temperature controller to 70° C. When the temperature of the mixture reached 70° C., 0.299 gm (0.0044) of sodium ethoxide (obtained from the Fluka Chemical Corporation of Milwaukee, Wis.) was added to the rbf. The set point on the temperature controller was increased to 90° C. Once the reaction mixture reaches 85° C. volatiles generated is collected in the Dean-Stark adapter. The reaction mixture was stopped once the volatiles stopped collecting in the Dean-Stark (5.0 mL). The reaction was cooled and analyzed by GPC and $^1$HNMR. Final product was a dark brown viscous liquid. GPC data: 15.8% oligomerallylester (n=4), 13.4% tetramer allyl ester (n=3), 20.1% trimer allyl ester (n=2), 27.5% mono allylester, and 23.1% EtLPK.

Example 12

A 250 ml 4-neck round bottom flask was charged with 43.62 g (0.2 mol) EtLGK synthesized according to the method of Example 9 and 80.90 g (0.4 mol) of diethyl adipate (obtained from the Sigma Aldrich Company of St. Louis, Mo., and distilled prior to use). The flask was equipped with a mechanical stirrer, thermocouple, and an inlet for nitrogen and outlet to a bubbler. The contents of the flask were heated to 60° C. on a heating mantle, and purged with nitrogen to dry the reactor contents until the water concentration of the flask contents was less than 100 ppm as determined by Karl Fischer titration. The flask was then equipped with a Dean Stark trap, condenser, and a firestone valve which allowed for either vacuum or nitrogen to enter the system. Next 12.02 μl of titanium tetra-isopropoxide (obtained from Acros Organics of Geel, Belgium) was added to the reaction flask via a microliter syringe. The contents of the flask were then heated to 110° C. Then the reaction was degassed by applying a vacuum of 3 to 5 Torr to the reaction flask for 5 min. While under vacuum, the glassware was flame-dried to eliminate any additional moisture in the system. After pulling vacuum, the reaction flask was back filled with nitrogen for 5 min. This process was repeated three times.

The contents of the flask were then heated to 230° C. under constant nitrogen purging. A liquid was observed to collect in the Dean Stark trap; the rate of collection was monitored to determine the rate of conversion of the condensation reaction. After about 160 minutes of collecting liquid, the heat was shut off and the contents of the flask were allowed to cool to ambient temperature. The conversion had reached >99% by measuring the amount of residual EtLGK in the reactor by GC-FID. The reaction mixture was subsequently distilled under vacuum to remove volatiles until the level of EtLGK and diethyl adipate in the final product was below 1%. The final reaction composition, as determined by GPC, was approximately 45% of the 1:1 adduct of adipate:LGK, 27% 1:2 adipate:LGK adduct, 27% 1:3 adipate:LGK and higher oligomers, and 1% combined total of diethyl adipate and EtLGK.

Example 13

A 3-neck round bottom flask (rbf) was charged with 57.55 gm (0.13 moles) of the product of Example 12. The rbf was equipped with a thermocouple fitted using an adapter, a Dean- Stark fitted with a condenser, an adapter for nitrogen purge and Teflon coated magnetic spindle for stirring. Nitrogen purge was started in the rbf and the stirrer was set at 500 rpm. Then 31.82 mL (0.47 moles) of allyl alcohol (obtained from the Sigma-Aldrich Company of St. Louis, Mo.) was carefully added to the rbf using a 30 mL syringe. The rbf was heated using a heating mantle connected to a temperature controller to 70° C. When the temperature of the mixture reached 70° C., 0.424 gm (0.0062 moles) of sodium ethoxide (obtained from the Fluka Chemical Corporation of Milwaukee, Wis.) was added to the rbf. The set point on the temperature controller was increased to 90° C. Once the reaction mixture reaches 85° C. volatiles generated is collected in the Dean-Stark adapter. The reaction mixture was stopped once the volatiles stopped collecting in the Dean-Stark (17.5 mL). The reaction was cooled and analyzed by GPC. The sodium ethoxide was neutralized by adding 4.1 gm (0.031 moles) of ammonium sulfate to the reaction mixture and heating it to 100° C. under 80-90 torr vacuum for about 1 hour. Then the pH of the reaction mixture was measured (pH=8.9). The solids were removed by filtration using a Millipore filter (0.45 μm, HNWP Millipore, Ireland). Volatiles were distilled out using a short path distillation column under 0.5 torr vacuum while heating the flask in an oil bath set to 220° C. The final product was a dark brown viscous liquid that was analyzed by GPC. GPC data: 14.4% oligomeric diallyl ester (n=3), 21.6% trimer diallyl ester (n=2), 43.9% mono diallyl ester (n=1), and 0.96% LGK allyl ester.

Example 14

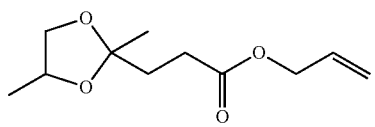

A 3-neck round bottom flask (rbf) was charged with 36.86 gm (0.182 moles) of EtLPK. The rbf was equipped with a thermocouple fitted using an adapter, a Dean-Stark fitted with a condenser, an adapter for nitrogen purge and Teflon coated magnetic spindle for stirring. Nitrogen purge was started in the rbf and the stirrer was set at 300 rpm. Then 15.5 mL (0.273 moles) of allyl alcohol (obtained from the Sigma-Aldrich Company of St. Louis, Mo.) was carefully added to the rbf using a 20 mL syringe. The rbf was heated using a heating mantle connected to a temperature controller to 70° C. When the temperature of the mixture reached 70° C., 0.261 gm (0.0038 moles) of sodium ethoxide (obtained from the Fluka Chemical Corporation of Milwaukee, Wis.) was added to the rbf. The set point on the temperature controller was increased to 90° C. Once the reaction mixture reaches 85° C. volatiles generated were collected in the Dean-Stark adapter. The reaction mixture was stopped once the volatiles stopped collecting in the Dean-Stark (4.0 mL). Sodium ethoxide (was neutralized by adding 2.53 gm (0.019 moles) ammonium sulfate to the reaction mixture and heating it to 60° C. under 80-90 torr vacuum for 1 hour. The solids were then removed by filtration using a Millipore filter (0.45 μm, HNWP Millipore, Ireland). The reaction was cooled and analyzed by GC-MS. Final product was a light yellow liquid. GC-MS data: 60% of the allyl ester.

Example 15

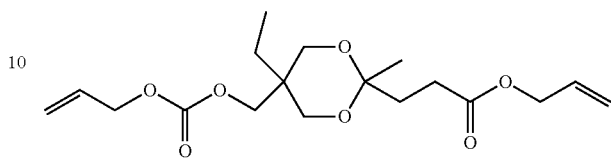

A 3-neck round bottom flask (rbf) was charged with 13.78 gm (0.04 moles) of product of Example 6. The rbf was equipped with a thermocouple fitted using an adapter, a Dean-Stark fitted with a condenser, an adapter for nitrogen purge and Teflon coated magnetic spindle for stirring. Nitrogen purge was started in the rbf and the stirrer was set at 400 rpm. Then 4.08 mL (0.06 moles) of allyl alcohol (obtained from the Sigma-Aldrich Company of St. Louis, Mo.) was carefully added to the rbf using a 5.0 mL syringe. The rbf was heated using an oil bath which was heated to 100° C. 0.086 gm (0.0013 moles) of sodium ethoxide (obtained from the Fluka Chemical Corporation of Milwaukee, Wis.) was added to the rbf. No volatiles were generated. The oil bath was heated to 107° C. and after 30 mins the reaction mixture was subjected to full vacuum, around 50 torr. The reaction mixture started boiling vigorously, so that vacuum pump was switched off and the rbf was back filled with nitrogen. The reaction mixture was stopped once the volatiles had stopped collecting (<1.0 mL). The reaction was cooled and analyzed by GC-MS. GC-MS showed a mixture of products. The yield of the diallyl derivative was 9.0%. There was also 22.25% of the allyl compound structure shown below:

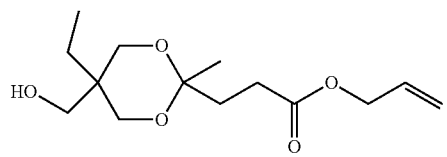 [SMILES: C=CCOC(=O)CCC1(C)OCC(CC)(CO)CO1]

Example 16

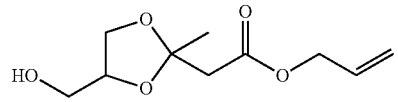

A 3-neck round bottom flask (rbf) was charged with 20.42 gm (0.1 moles) of EtAGK synthesized as in Example 7. The rbf was equipped with a thermocouple fitted using an adapter, a Dean-Stark fitted with a condenser, an adapter for nitrogen purge and Teflon coated magnetic spindle for stirring. Nitrogen purge was started in the rbf and the stirrer was set at 300 rpm. Then 17.0 mL (0.25 moles) of allyl alcohol (obtained from the Sigma-Aldrich Company of St. Louis, Mo.) was carefully added to the rbf using a 5.0 mL syringe. The rbf was heated using an oil bath which was heated to 100° C. 0.175 gm (0.0026 moles) of sodium ethoxide (obtained from the Fluka Chemical Corporation of Milwaukee, Wis.) was added to the rbf. The reaction mixture was stopped once the volatiles had stopped collecting (5.5 mL). The reaction was cooled and analyzed by GC-MS. GC-MS data showed 60% of the allyl ester.

Example 17

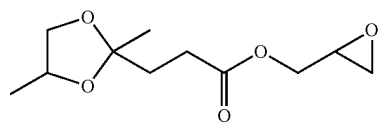 [SMILES: CC1COC(C)(CCC(=O)OCC2CO2)O1]

A single-neck round bottom flask (rbf) was charged with 1.01 gm (0.0046 moles) of the product of Example 14 and 10.0 mL of acetonitrile (obtained from Fisher Scientific of Waltham, Mass.), followed by addition of 1.5 gm (0.0087 moles) 85% m-chloroperoxybenzoic acid (obtained from the Sigma-Aldrich Company of St. Louis, Mo.). The rbf was equipped with a condenser and placed in an oil bath set at 85° C. The contents of the flask were refluxed for about 9 hrs. A white precipitated formed after the reaction was cooled to room temperature. The precipitate was filtered using Millipore filter (0.45 μm, HNWP Millipore, Ireland) and washed with 10 mL acetonitrile; the wash was added to the liquids. Acetonitrile was stripped from the flask by rotary evaporation. The final product was a clear liquid that was analyzed by GC-MS. Yield by GC-MS was 32% of the glycidyl ester.

Example 18

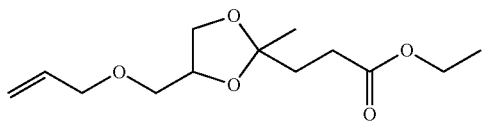 [SMILES: C=CCOCC1COC(C)(CCC(=O)OCC)O1]

A 3-neck round bottom flask (rbf) was charged with 43.66 gm (0.15 moles) of EtLGK, synthesized according to the procedure of Example 9. The rbf was equipped with a thermocouple fitted using an adapter, a condenser, an adapter for nitrogen purge and Teflon coated magnetic spindle for stirring. Nitrogen purge was started in the rbf and the stirrer was set at 400 rpm. The rbf was heated to 70° C. using a heating mantle and the EtLGK was dried under vacuum (5-7 torr) for about 1 hour. Then 25.4 mL (0.3 moles) of allyl bromide (obtained from the Sigma-Aldrich Company of St. Louis, Mo.) was added to the rbf with stirring, using a 30.0 mL syringe. After about 15 minutes of stirring under nitrogen, 41.46 gm (0.3 moles) of $K_2CO_3$ (obtained from Acros Organics of Geel, Belgium) was added. The temperature of the reaction mixture was increased to 125° C. and were maintained at this temperature with stirring for about 22 hours. The contents of the flask were allowed to cool to ambient temperature. A white precipitate was observed in the flask. The precipitate was filtered using a Millipore filter (0.45 μm, HNWP Millipore, Ireland) and the liquid remainder was analyzed by GC-MS, which showed 27.5% yield of the allyl ether EtLGK.

Example 19

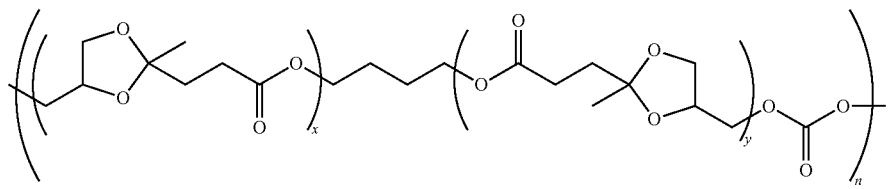

Figure 7:
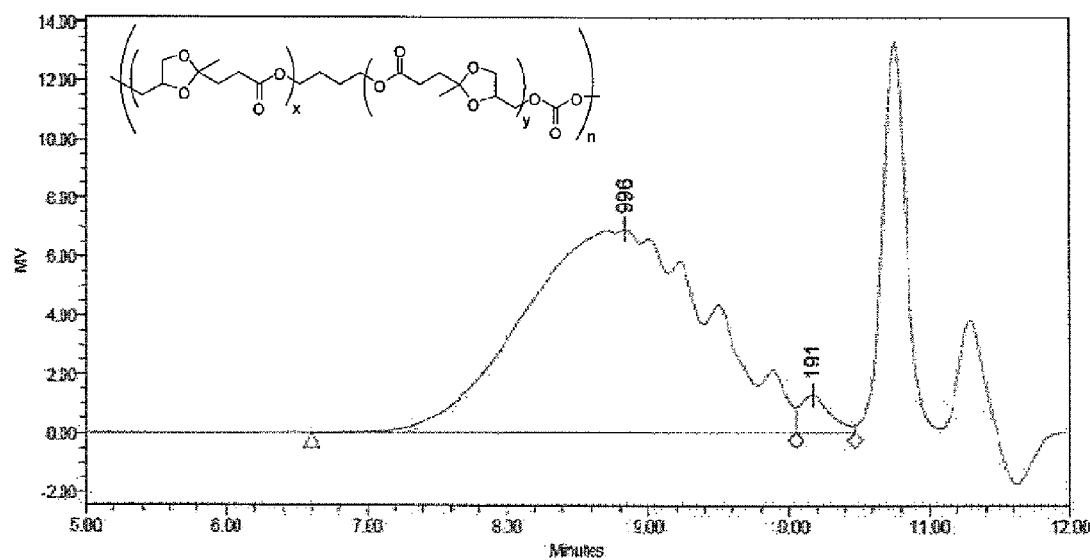
FIG. 7 shows a gel permeation chromatograph for a compound of the invention.
Figure 8:
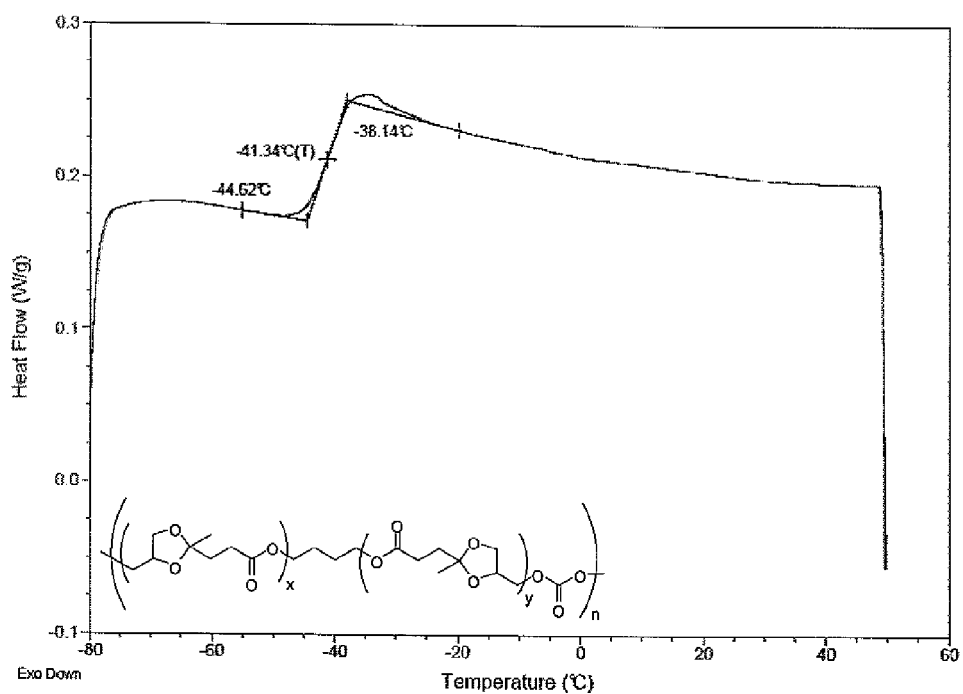
FIG. 8 shows a differential scanning calorimetry plot for a compound of the invention.

A 3-neck round bottom flask (rbf) was charged with 50.71 gm (0.11 moles) of the product of Example 12. The rbf was equipped with a thermocouple fitted using an adapter, a Dean-Stark trap with a condenser, an adapter for nitrogen purge and overhead mechanical stirrer with a stir shaft connected using an adapter and Teflon sleeve. Nitrogen purge and stirring were started in the rbf. The rbf was heated to 70° C. using a heating mantle, and vacuum of about 7-9 torr was applied with stirring, while the temperature was maintained for about 1 hour. Then 12.2 mL (0.1 moles) of diethyl carbonate (obtained from the Sigma-Aldrich Company of St. Louis, Mo.) was added to the reaction mixture using a 20 mL syringe. After about 10 minutes, 0.04 gm (0.0055 moles) of solid NaOEt (obtained from the Fluka Chemical Corporation of Milwaukee, Wis.) was added to the flask. The temperature of the contents of the flask was increased to 150° C. and was maintained at that temperature while a liquid was observed to collect in the Dean-Stark trap. The reaction mixture was removed from the heating mantle and allowed to cool to ambient temperature when liquid collection stopped. About 3.0 mL total liquid was collected. The contents of the flask were analyzed by GPC and $^1$H NMR. The product was a dark brown viscous liquid. GPC data (PS std): Mw=1364 (PDI=1.63), 2.88% EtLGK; Tg (DSC)=−41.3° C. The GPC is shown in FIG. 7 and the DSC is shown in FIG. 8.

Example 20

A 3-neck round bottom flask (rbf) was charged with 6.0 gm (0.0133 moles) of the product of Example 13 and 36.0 mL of $CHCl_3$ followed by addition of 9.5 gm (0.047 moles) 85% m-chloroperoxybenzoic acid (obtained from the Sigma-Aldrich Company of St. Louis, Mo.). The rbf was equipped with a condenser, thermocouple fitted with an adapter and a glass stopper. The rbf was heated to reflux using a heating mantle. Reflux was continued for about 16 hours, then the contents of the flask were allowed to cool to ambient temperature. A white precipitate formed after the reaction was cooled. The precipitate was removed by filtration and washed with 35 mL CHCl$_3$. The liquid contents of the flask were washed twice with 10 mL aliquots of 1 N NaOH followed by 10 mL water and the 10 mL saturated NaCl solution. The washed product was dried with Na$_2$SO$_4$ and filtered. The CHCl$_3$ was removed using rotary evaporation. The final product was a clear liquid that was analyzed by GPC and $^1$H NMR. Yield by GPC was 40% of diepoxide of the product of Example 13.

Example 21

A 1-neck round bottom flask (rbf) was charged with 3.64 gm (0.0081 moles) of the diepoxide product of Example 20 and 1.41 gm (0.012 moles) 1,6-hexamethylenediamine (obtained from the Sigma-Aldrich Company of St. Louis, Mo., distilled prior to use). The rbf was equipped with magnetic stir bar and nitrogen purge and was heated using a temperature controlled oil bath 140° C. Nitrogen purge was started in the rbf and the magnetic stirrer was set at 400 rpm. The contents of the flask were heated immersed in the oil bath until the temperature reached 140° C., then the flask was removed from the oil bath and the contents allowed to cool to ambient temperature. The contents of the flask were analyzed by DSC and TGA. Final product was a dark brown viscous liquid. Tg (DSC)=−20.3° C.

Example 22

Figure 9:
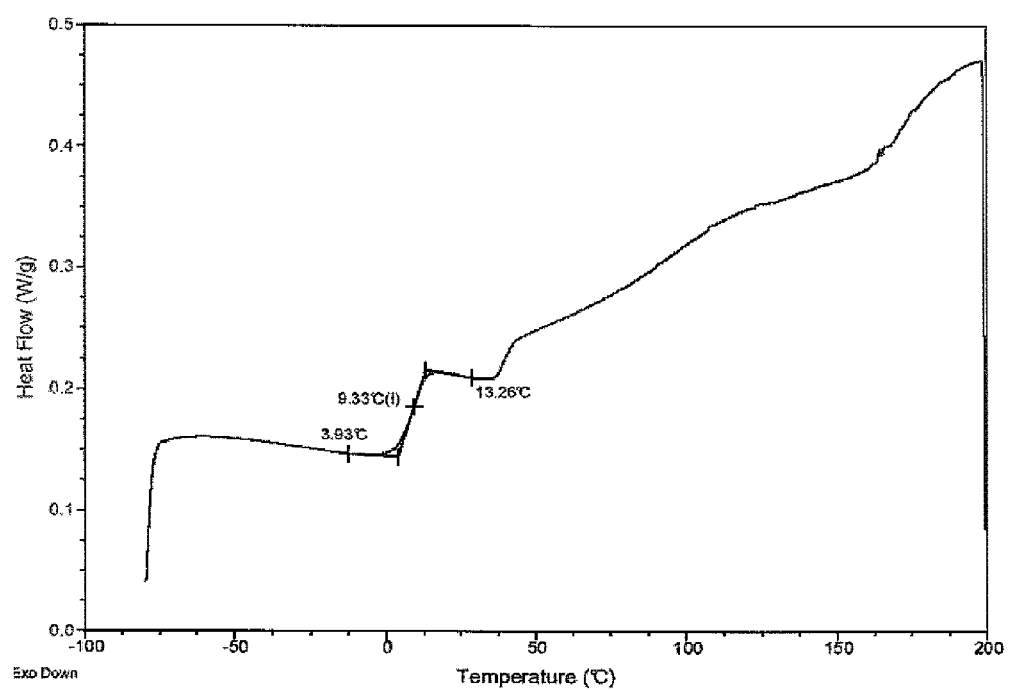
FIG. 9 shows a differential scanning calorimetry plot for a compound of the invention.

A 250-mL disposable cup was charged with 9.98 gm of the product of Example 19. Using a microliter syringe, 23 µl (0.25 parts per 100 parts polyol) of dibutyltin dilaurate (98%, obtained from Pfaltz and Bauer, Inc. of Waterbury, Conn.) was added to the cup. Using a microliter syringe, 24 µl (0.25 parts per 100 parts polyol) of triethylenediamine (DABCO 33LV, obtained from Air Products and Chemicals, Inc. of Allentown, Pa.) was added to the cup and hand-mixed with a tongue depressor until homogeneous. Then 2.08 gm (103% isocyanate index) toluenediisocyanate (Mondor TD-80, obtained from Bayer MaterialScience of Hong Kong, P.R. China) was weighed into the cup and hand-mixed until homogeneous. The cup was allowed to sit in a fume hood overnight. The sample was found to be soluble in methylene chloride and insoluble in hexane. The product was analyzed by DSC; Tg=9.33° C. The DSC of the product is shown in FIG. 9.

Example 23

Figure 10:
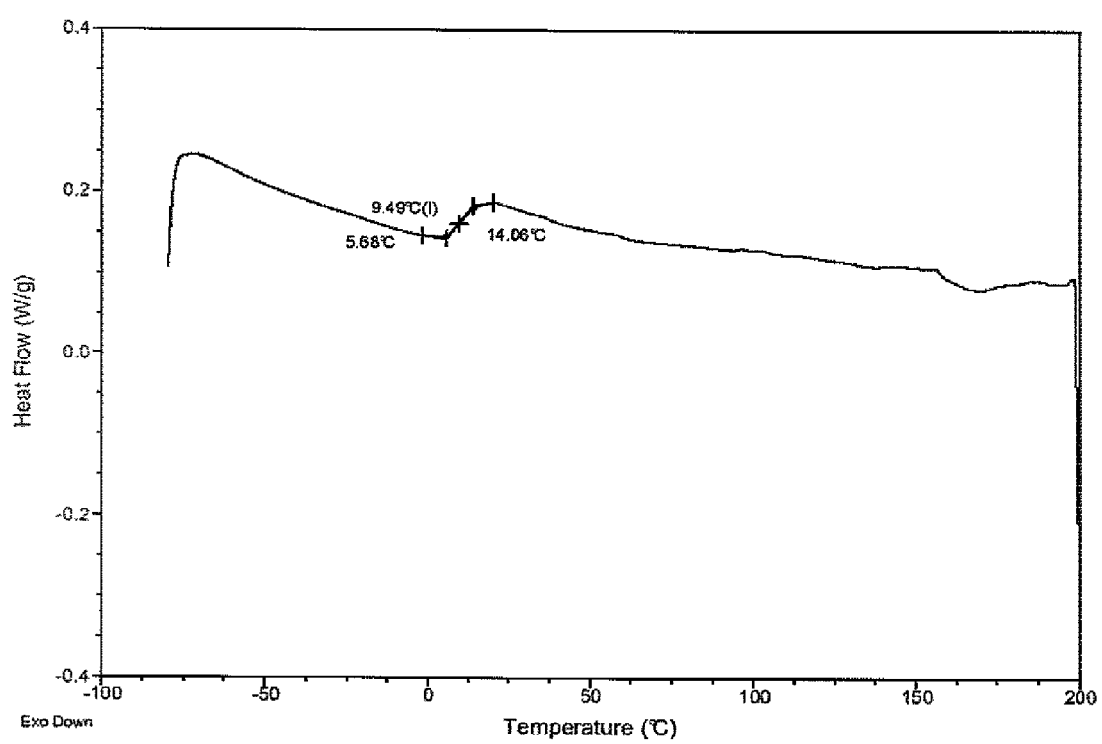
FIG. 10 shows a differential scanning calorimetry plot for a compound of the invention.

A 250-mL disposable cup was charged with 9.98 gm Example 19 using a microliter syringe, 23 µl (0.25 parts per 100 parts polyol) of dibutyltin dilaurate (98%, obtained from Pfaltz and Bauer, Inc. of Waterbury, Conn.) was added to the cup. Again using a micro syringe, 24 µl (0.25 parts per 100 parts polyol) of triethylenediamine catalyst (DABCO 33LV, obtained from Air Products and Chemicals, Inc. of Allentown, Pa.) was added to the cup and hand-mixed with a tongue depressor until homogeneous. 3.13 gm (103% isocyanate index) polymeric MDI (PAPI 94, obtained from the Dow Chemical Company of Midland, Mich.) was weighed into the cup and hand-mixed until homogeneous. The cup was allowed to sit in a fume hood overnight. The contents of the cup were found to be slightly soluble in methylene chloride and insoluble in hexane. The contents of the cup were analyzed by DSC; Tg=9.49° C. The DSC of the product is shown in FIG. 10.

The various embodiments described above are provided by way of illustration only and should not be construed to limit the claims attached hereto. The present invention may suitably comprise, consist of, or consist essentially of, any of the disclosed or recited elements. Thus, the invention illustratively disclosed herein can be suitably practiced in the absence of any element which is not specifically disclosed herein. Various modifications and changes will be recognized that may be made without following the example embodiments and applications illustrated and described herein, and without departing from the true spirit and scope of the following claims.

The invention claimed is:

1. A polycarbonate one or more repeat units IA, IB, or a combination thereof:

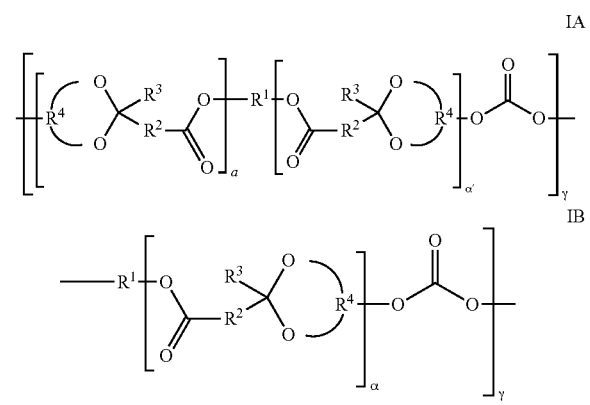

wherein
R$^1$ is a divalent linear, branched, or cyclic alkyl group having 1 to 36 carbon atoms, a linear or branched alkenyl group having 1 to 36 carbon atoms, an aryl group, or an alkaryl group having from 7 to 36 carbon atoms;
R$^2$ is a covalent bond or a linear, branched, or cyclic alkyl group having 1 to 18 carbon atoms, a linear or branched alkenyl group having 1 to 18 carbon atoms, an aryl group, or an alkaryl group having from 7 to 18 carbon atoms;
R$^3$ is hydrogen, alkynyl, or a linear, branched, or cyclic alkyl group having 1 to 18 carbon atoms, a linear or branched alkenyl group having 1 to 18 carbon atoms, an aryl group, or an alkaryl group having from 7 to 18 carbon atoms;
R$^4$ is a group having the formula

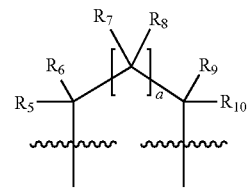

wherein
a is 0 or 1 and
R$^5$, R$^6$, R$^7$, R$^8$, R$^9$, and R$^{10}$ are independently hydrogen, alkynyl, or linear, branched, or cyclic alkyl groups having 1 to 18 carbon atoms, linear or branched alkenyl groups having 1 to 18 carbon atoms, aryl groups, or alkaryl groups having from 7 to 18 carbon atoms;
α and α' are independently integers of 1 to about 100; and
γ is an integer of 1 to about 30 and γ is the same or different for repeat unit IA and repeat unit IB.

2. The polycarbonate of claim 1 wherein $R^1$ further comprises one or more functional groups comprising halogen, tertiary amine, hydroxyl, carbonate, carboxylic acid, carboxylic ester, ether, carbonyl, ketal, urethane, imide, amide, or a combination thereof.

3. The polycarbonate of claim 1 wherein repeating units IA, IB, or both further comprise hydroxyl functional endgroups.

4. The polycarbonate of claim 1 wherein one or more $\alpha$, $\alpha'$, or both are independently between 0 and about 5.

5. The polycarbonate of claim 1 wherein $R^2$ is —$(CH_2)_2$—, and $R^3$ is —$CH_3$, and $R^4$ is the residue of glycerol.

6. The polycarbonate of claim 1 wherein about 25% by weight or more of the compound is biomass based.

7. The polycarbonate of claim 1 wherein between about 25% and 90% by weight of the compound is biomass based.

8. The polycarbonate of claim 1 wherein between about 40% and 75% by weight of the compound is biomass based.

9. The polycarbonate of claim 1 wherein the compound is biodegradable.

10. The polycarbonate of claim 1 wherein one or more values of $\gamma$ is between about 1 and 10 and repeat units IA, IB, or both further comprise hydroxyl functional endgroups.

11. The polycarbonate of claim 1, wherein one or more $\gamma$ is between about 1 and 10 and repeat units IA, IB, or both further comprise one or more repeat units comprising a polyurethane moiety.

12. The polycarbonate of claim 1 wherein
$R^2$ is —$(CH_2)_2$—, $R^3$ is —$CH_3$, and $R^4$ is the residue of glycerol; and
one or more $\alpha$, $\alpha'$, or both are independently between 0 and about 5.

13. The polycarbonate of claim 12 wherein repeat units IA, IB, or both further comprise hydroxyl functional endgroups.

\* \* \* \* \*